(12) United States Patent
Jung et al.

(10) Patent No.: US 8,927,232 B2
(45) Date of Patent: Jan. 6, 2015

(54) FUSION PROTEIN CAPABLE OF BINDING VEGF-A AND TNF-ALPHA

(75) Inventors: Keehoon Jung, Seoul (KR); Young Jun Koh, Deajeon (KR); Gyun Min Lee, Daejeon (KR); Sun Chang Kim, Daejeon (KR); Gou Young Koh, Daejeon (KR)

(73) Assignee: Korea Advanced Institute of Science and Technology (KAIST), Daejeon (KR)

( * ) Notice: Subject to any disclaimer, the term of this patent is extended or adjusted under 35 U.S.C. 154(b) by 501 days.

(21) Appl. No.: 12/636,013

(22) Filed: Dec. 11, 2009

(65) Prior Publication Data

US 2010/0150926 A1 Jun. 17, 2010

Related U.S. Application Data

(60) Provisional application No. 61/121,868, filed on Dec. 11, 2008.

(51) Int. Cl.
| | |
|---|---|
| A61K 38/17 | (2006.01) |
| C07K 14/71 | (2006.01) |
| C07K 14/715 | (2006.01) |
| C12N 5/10 | (2006.01) |
| C12N 15/12 | (2006.01) |

(52) U.S. Cl.
CPC ............ *C07K 14/71* (2013.01); *C07K 14/715* (2013.01); *C07K 2319/70* (2013.01)
USPC ......... 435/69.7; 514/8.1; 514/20.8; 514/16.6; 514/13.3; 530/350; 530/402; 435/320.1; 435/252.3; 435/254.11; 435/326

(58) Field of Classification Search
None
See application file for complete search history.

(56) References Cited

U.S. PATENT DOCUMENTS

| | | | |
|---|---|---|---|
| 5,637,481 A | * | 6/1997 | Ledbetter et al. |
| 2004/0014948 A1 | * | 1/2004 | Halkier et al. |
| 2007/0166788 A1 | * | 7/2007 | Jin et al. |

FOREIGN PATENT DOCUMENTS

WO WO 2005-113596 A2 12/2005

OTHER PUBLICATIONS

Chamow et al., Immunoadhesins: principles and applications, TIBTECH, 14:52-60, Feb. 1996.*
Chan et al., A domain in TNF receptors that mediates ligand-independent receptor assembly and signaling, Science, 288:2351-2354, Jun. 30, 2000.*
Holash et al., VEGF-trap: A VEGF blocker with potent antitumor effect, Proc. Nat. Acad. Sci. USA, 99(17):11393-11398, Aug. 20, 2002.*

(Continued)

*Primary Examiner* — Claire Kaufman
(74) *Attorney, Agent, or Firm* — Joseph H. Kim; JHK Law

(57) ABSTRACT

The present application describes an isolated nucleic acid molecule encoding a polypeptide capable of synchronously binding VEGF polypeptide and TNF polypeptide comprising: (a) a nucleotide sequence encoding a TNFR2 component and VEGFR1 component operatively linked to (b) a nucleotide sequence encoding a multimerizing component, wherein the TNFR2 component consists essentially of a nucleotide sequence encoding the amino acid sequences of cystein rich domain 1, cystein rich domain 2, cystein rich domain 3, and cystein rich domain 4 of the extracellular domain of TNFR2, and wherein the VEGFR1 component consists essentially of a nucleotide sequence encoding the amino acid sequences of Ig-like domain 2 of the extracellular domain of VEGFR1.

19 Claims, 22 Drawing Sheets

Anti-inflammatory angiogenic protein

Valpha: VEGF and TNF-alpha double blocker

Estimated Mw: 65 kD
Theoretical pI: 7.14

(56) References Cited

OTHER PUBLICATIONS

Ruegg, Curzio et al., "Antiangiogenic peptides and proteins: From experimental tools to clinical drugs," Biochimica et Biophysica Acta, vol. 1765: 155-177, Oct. 7, 2005, online publication.

Zhang, Rong et al., "Etk/Bmx Transactivates Vascular Endothelial Growth Factor 2 and Recruits Phosphatidylinositol 3-Kinase to Mediate the Tumor Necrosis Factor-induced Angiogenic Pathway," JBC, vol. 278(51): 51267-51276, Dec. 19, 2003.

Temming, Kai et al., "RGD-based strategies for selective delivery of therapeutics and imaging agents to the tumor vasculature," Drug Resist Updat., 8(6): 381-402, Dec. 2005.

* cited by examiner

Protein expression and secretion

Protein purification and isoelectric focusing of Valpha

Figure 13
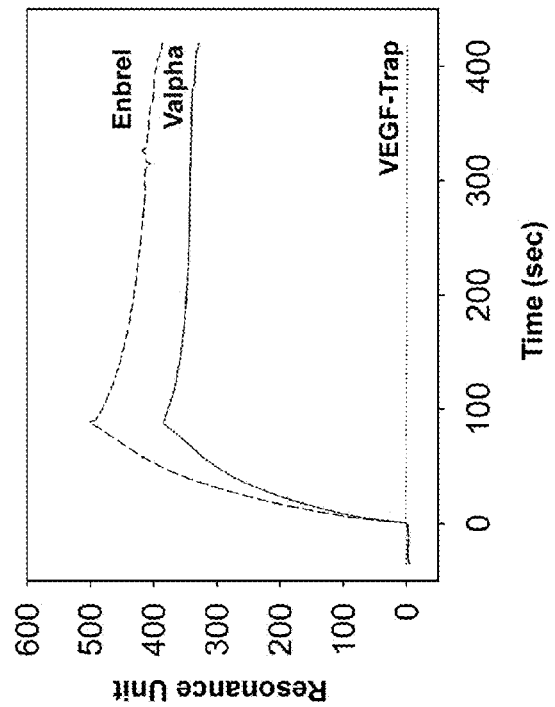
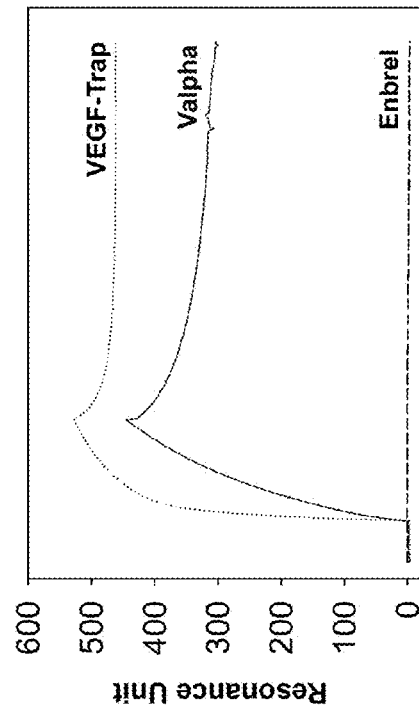

Figure 16
TNF-α-induced cytotoxicity
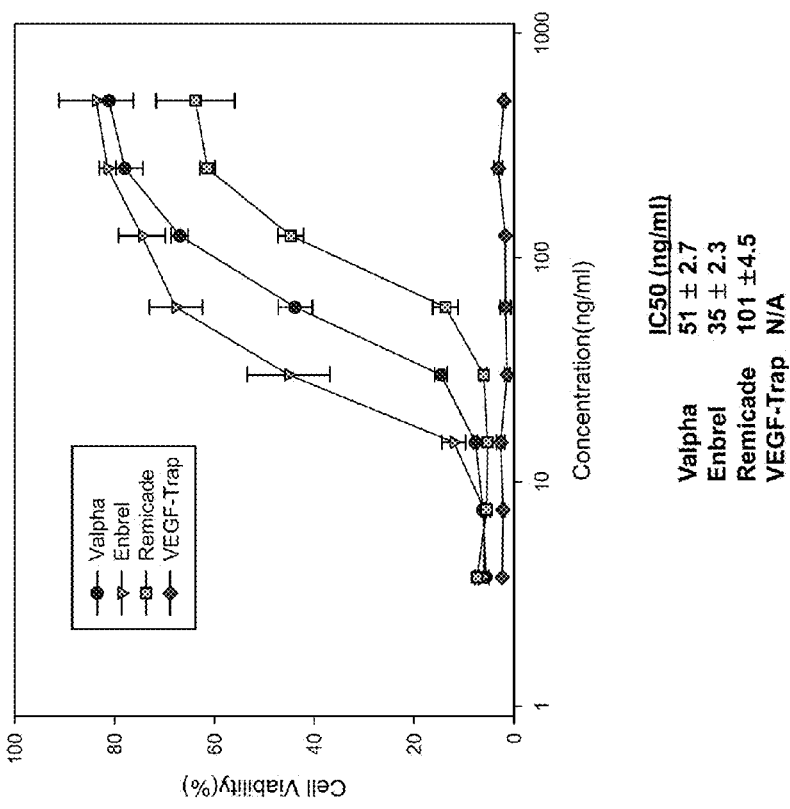
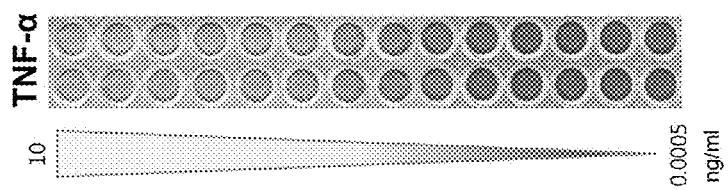

Figure 18
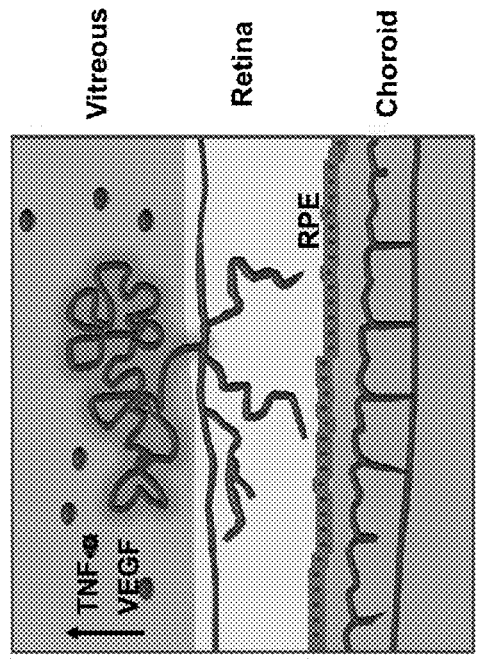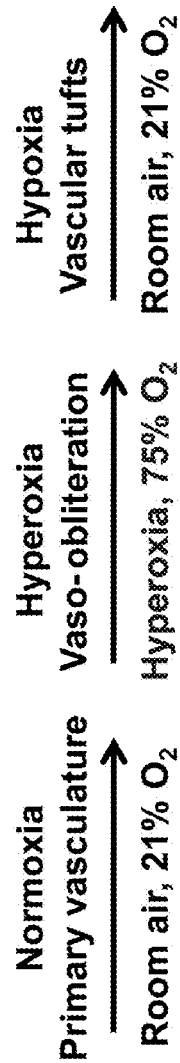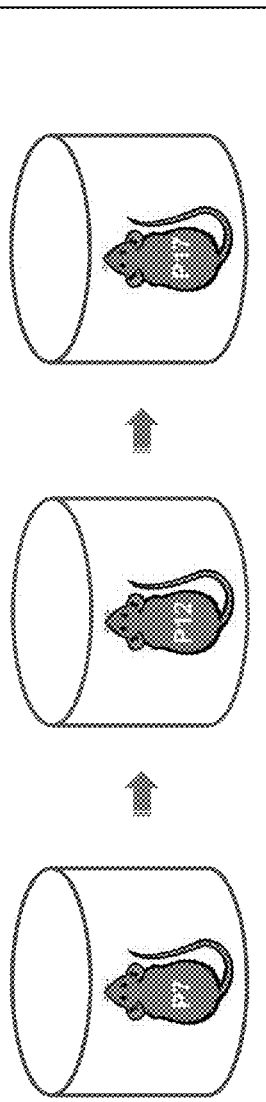

Valpha inhibited abnormal preretinal tufts formation in retinopathy

The effects of Valpha on suppression of bone destruction in CIA

SEQUENCE LISTING

<160> NUMBER OF SEQ ID NOS: 4

<210> SEQ ID NO 1
<211> LENGTH: 1743
<212> TYPE: DNA
<213> ORGANISM: Artificial Sequence
<220> FEATURE:
<223> OTHER INFORMATION: Valpha FV#1

<400> SEQUENCE: 1

| | | | | | | |
|---|---|---|---|---|---|---|
| atggcgcccg | tcgccgtctg | ggccgcgctg | gccgtcggac | tggagctctg | ggctgcggcg | 60 |
| cacgccttgc | cgcccaggt | ggcatttaca | ccctacgccc | cggagcccgg | gagcacatgc | 120 |
| cggctcagag | aatactatga | ccagacagct | cagatgtgct | gcagcaaatg | ctcgccgggc | 180 |
| caacatgcaa | aagtcttctg | taccaagacc | tcggacaccg | tgtgtgactc | ctgtgaggac | 240 |
| agcacataca | cccagctctg | gaactgggtt | cccgagtgct | tgagctgtgg | ctcccgctgt | 300 |
| agctctgacc | aggtggaaac | tcaagcctgc | actcgggaac | agaaccgcat | ctgcacctgc | 360 |
| aggcccggct | ggtactgcgc | gctgagcaag | caggaggggt | gccggctgtg | cgcgccgctg | 420 |
| cgcaagtgcc | gcccgggctt | cggcgtggcc | agaccaggaa | ctgaaacatc | agacgtggtg | 480 |
| tgcaagccct | gtgccccggg | gacgttctcc | aacacgactt | catccacgga | tatttgcagg | 540 |
| ccccaccaga | tctgtaacgt | ggtggccatc | cctgggaatg | caagcatgga | tgcagtctgc | 600 |
| acgtccacgt | cccccacccg | gagtatggcc | ccaggggcag | tacacttacc | ccagccagtg | 660 |
| tccacacgat | cccaacacac | gcagccaact | ccagaaccca | gcactgctcc | aagcacctcc | 720 |
| ttcctgctcc | caatgggccc | cagccccca | gctgaaggga | gcactggcga | cggtagacct | 780 |
| ttcgtagaga | tgtacagtga | aatccccgaa | attatacaca | tgactgaagg | aagggagctc | 840 |
| gtcattccct | gccgggttac | gtcacctaac | atcactgtta | cttttaaaaa | gtttccactt | 900 |
| gacactttga | tccctgatgg | aaaacgcata | atctgggaca | gtagaaaggg | cttcatcata | 960 |
| tcaaatgcaa | cgtacaaaga | aatagggctt | ctgacctgtg | aagcaacagt | caatgggcat | 1020 |
| ttgtataaga | caaactatct | cacacatcga | caactcgagg | acaaaactca | cacatgccca | 1080 |
| ccgtgcccag | cacctgaact | cctgggggga | ccgtcagtct | tcctcttccc | cccaaaaccc | 1140 |
| aaggacaccc | tcatgatctc | ccggaccct | gaggtcacat | gcgtggtggt | ggacgtgagc | 1200 |
| cacgaagacc | ctgaggtcaa | gttcaactgg | tacgtggacg | gcgtggaggt | gcataatgcc | 1260 |
| aagacaaagc | cgcgggagga | gcagtacaac | agcacgtacc | gtgtggtcag | cgtcctcacc | 1320 |
| gtcctgcacc | aggactggct | gaatggcaag | gagtacaagt | gcaaggtctc | caacaaagcc | 1380 |
| ctcccagccc | ccatcgagaa | aaccatctcc | aaagccaaag | ggcagccccg | agaaccacag | 1440 |
| gtgtacaccc | tgcccccatc | ccgggaggag | atgaccaaga | accaggtcag | cctgacctgc | 1500 |
| ctggtcaaag | gcttctatcc | cagcgacatc | gccgtggagt | gggagagcaa | tgggcagccg | 1560 |
| gagaacaact | acaagaccac | gcctcccgtg | ctggactccg | acggctcctt | cttcctctac | 1620 |
| agcaagctca | ccgtggacaa | gagcaggtgg | cagcagggga | acgtcttctc | atgctccgtg | 1680 |
| atgcatgagg | ctctgcacaa | ccactacacg | cagaagagcc | tctccctgtc | tccgggtaaa | 1740 |
| tga | | | | | | 1743 |

<210> SEQ ID NO 2
<211> LENGTH: 580
<212> TYPE: PRT
<213> ORGANISM: Artificial Sequence
<220> FEATURE:
<223> OTHER INFORMATION: Valpha FV#1

<400> SEQUENCE: 2

```
Met Ala Pro Val Ala Val Trp Ala Ala Leu Ala Val Gly Leu Glu Leu
1               5                   10                  15

Trp Ala Ala Ala His Ala Leu Pro Ala Gln Val Ala Phe Thr Pro Tyr
            20                  25                  30

Ala Pro Glu Pro Gly Ser Thr Cys Arg Leu Arg Glu Tyr Tyr Asp Gln
        35                  40                  45

Thr Ala Gln Met Cys Cys Ser Lys Cys Ser Pro Gly Gln His Ala Lys
    50                  55                  60

Val Phe Cys Thr Lys Thr Ser Asp Thr Val Cys Asp Ser Cys Glu Asp
65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
            100                 105                 110

Glu Gln Asn Arg Ile Cys Thr Cys Arg Pro Gly Trp Tyr Cys Ala Leu
        115                 120                 125

Ser Lys Gln Glu Gly Cys Arg Leu Cys Ala Pro Leu Arg Lys Cys Arg
    130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220

Gln His Thr Gln Pro Thr Pro Glu Pro Ser Thr Ala Pro Ser Thr Ser
225                 230                 235                 240

Phe Leu Leu Pro Met Gly Pro Ser Pro Ala Glu Gly Ser Thr Gly
                245                 250                 255

Asp Gly Arg Pro Phe Val Glu Met Tyr Ser Glu Ile Pro Glu Ile Ile
            260                 265                 270

His Met Thr Glu Gly Arg Glu Leu Val Ile Pro Cys Arg Val Thr Ser
        275                 280                 285

Pro Asn Ile Thr Val Thr Leu Lys Lys Phe Pro Leu Asp Thr Leu Ile
    290                 295                 300

Pro Asp Gly Lys Arg Ile Ile Trp Asp Ser Arg Lys Gly Phe Ile Ile
305                 310                 315                 320

Ser Asn Ala Thr Tyr Lys Glu Ile Gly Leu Leu Thr Cys Glu Ala Thr
                325                 330                 335

Val Asn Gly His Leu Tyr Lys Thr Asn Tyr Leu Thr His Arg Gln Leu
            340                 345                 350

Glu Asp Lys Thr His Thr Cys Pro Pro Cys Pro Ala Pro Glu Leu Leu
        355                 360                 365

Gly Gly Pro Ser Val Phe Leu Phe Pro Pro Lys Pro Lys Asp Thr Leu
    370                 375                 380

Met Ile Ser Arg Thr Pro Glu Val Thr Cys Val Val Val Asp Val Ser
385                 390                 395                 400

His Glu Asp Pro Glu Val Lys Phe Asn Trp Tyr Val Asp Gly Val Glu
```

```
            405                 410                 415
Val His Asn Ala Lys Thr Lys Pro Arg Glu Glu Gln Tyr Asn Ser Thr
            420                 425                 430

Tyr Arg Val Val Ser Val Leu Thr Val Leu His Gln Asp Trp Leu Asn
            435                 440                 445

Gly Lys Glu Tyr Lys Cys Lys Val Ser Asn Lys Ala Leu Pro Ala Pro
            450                 455                 460

Ile Glu Lys Thr Ile Ser Lys Ala Lys Gly Gln Pro Arg Glu Pro Gln
465                 470                 475                 480

Val Tyr Thr Leu Pro Pro Ser Arg Glu Glu Met Thr Lys Asn Gln Val
            485                 490                 495

Ser Leu Thr Cys Leu Val Lys Gly Phe Tyr Pro Ser Asp Ile Ala Val
            500                 505                 510

Glu Trp Glu Ser Asn Gly Gln Pro Glu Asn Asn Tyr Lys Thr Thr Pro
            515                 520                 525

Pro Val Leu Asp Ser Asp Gly Ser Phe Phe Leu Tyr Ser Lys Leu Thr
            530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
            565                 570                 575

Ser Pro Gly Lys
            580

<210> SEQ ID NO 3
<211> LENGTH: 1755
<212> TYPE: DNA
<213> ORGANISM: Artificial Sequence
<220> FEATURE:
<223> OTHER INFORMATION: Valpha VF#1

<400> SEQUENCE: 3
atggtcagct actgggacac cggggtcctg ctgtgcgcgc tgctcagctg tctgcttctc      60
acaggatcta gttcaggtgg tagacctttc gtagagatgt acagtgaaat ccccgaaatt     120
atacacatga ctgaaggaag ggagctcgtc attccctgcc gggttacgtc acctaacatc     180
actgttactt taaaaaagtt tccacttgac actttgatcc ctgatggaaa acgcataatc     240
tgggacagta gaaagggctt catcatatca atgcaacgt acaaagaaat agggcttctg      300
acctgtgaag caacagtcaa tgggcatttg tataagacaa actatctcac acatcgacaa     360
ttgcccgccc aggtggcatt tacaccctac gccccgagc ccgggagcac atgccggctc      420
agagaatact atgaccagac agctcagatg tgctgcagca atgctcgcc gggccaacat      480 gcaaaagtct tctgtaccaa gacctcggac accgtgtgtg actcctgtga ggacagcaca     540
tacacccagc tctggaactg ggttcccgag tgcttgagct gtggctcccg ctgtagctct     600
gaccaggtgg aaactcaagc ctgcactcgg aacagaacc gcatctgcac ctgcaggccc      660
ggctggtact gcgcgctgag caagcaggag gggtgccggc tgtgcgcgcc gctgcgcaag     720
tgccgcccgg gcttcggcgt ggccagacca ggaactgaaa catcagacgt ggtgtgcaag     780
ccctgtgccc cggggacgtt ctccaacacg acttcatcca cggatatttg caggccccac     840
cagatctgta acgtggtggc catccctggg aatgcaagca tggatgcagt ctgcacgtcc     900 acgtcccca cccggagtat ggccccaggg cagtacact acccagcc agtgtccaca      960 cgatcccaac acacgcagcc aactccagaa cccagcactg ctccaagcac ctccttcctg    1020
```

-continued

```
ctcccaatgg gccccagccc cccagctgaa gggagcactg gcgacctcga ggacaaaact    1080
cacacatgcc caccgtgccc agcacctgaa ctcctggggg gaccgtcagt cttcctcttc    1140
cccccaaaac ccaaggacac cctcatgatc tcccggaccc ctgaggtcac atgcgtggtg    1200
gtggacgtga gccacgaaga ccctgaggtc aagttcaact ggtacgtgga cggcgtggag    1260
gtgcataatg ccaagacaaa gccgcgggag gagcagtaca acagcacgta ccgtgtggtc    1320
agcgtcctca ccgtcctgca ccaggactgg ctgaatggca aggagtacaa gtgcaaggtc    1380
tccaacaaag ccctcccagc ccccatcgag aaaaccatct ccaaagccaa agggcagccc    1440
cgagaaccac aggtgtacac cctgccccca tcccgggagg agatgaccaa gaaccaggtc    1500
agcctgacct gcctggtcaa aggcttctat cccagcgaca tcgccgtgga gtgggagagc    1560
aatgggcagc cggagaacaa ctacaagacc acgcctcccg tgctggactc cgacggctcc    1620
ttcttcctct acagcaagct caccgtggac aagagcaggt ggcagcaggg gaacgtcttc    1680
tcatgctccg tgatgcatga ggctctgcac aaccactaca cgcagaagag cctctccctg    1740
tctccgggta aatga                                                    1755
```

<210> SEQ ID NO 4
<211> LENGTH: 584
<212> TYPE: PRT
<213> ORGANISM: Artificial Sequence
<220> FEATURE:
<223> OTHER INFORMATION: Valpha VF#1

<400> SEQUENCE: 4

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
                20                  25                  30

Met Tyr Ser Glu Ile Pro Glu Ile Ile His Met Thr Glu Gly Arg Glu
            35                  40                  45

Leu Val Ile Pro Cys Arg Val Thr Ser Pro Asn Ile Thr Val Thr Leu
        50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110

Thr Asn Tyr Leu Thr His Arg Gln Leu Pro Ala Gln Val Ala Phe Thr
        115                 120                 125

Pro Tyr Ala Pro Glu Pro Gly Ser Thr Cys Arg Leu Arg Glu Tyr Tyr
    130                 135                 140

Asp Gln Thr Ala Gln Met Cys Cys Ser Lys Cys Ser Pro Gly Gln His
145                 150                 155                 160

Ala Lys Val Phe Cys Thr Lys Thr Ser Asp Thr Val Cys Asp Ser Cys
                165                 170                 175

Glu Asp Ser Thr Tyr Thr Gln Leu Trp Asn Trp Val Pro Glu Cys Leu
            180                 185                 190

Ser Cys Gly Ser Arg Cys Ser Ser Asp Gln Val Glu Thr Gln Ala Cys
        195                 200                 205

Thr Arg Glu Gln Asn Arg Ile Cys Thr Cys Arg Pro Gly Trp Tyr Cys
    210                 215                 220

Ala Leu Ser Lys Gln Glu Gly Cys Arg Leu Cys Ala Pro Leu Arg Lys
```

-continued

```
                225                 230                 235                 240
            Cys Arg Pro Gly Phe Gly Val Ala Arg Pro Gly Thr Glu Thr Ser Asp
                            245                 250                 255
            Val Val Cys Lys Pro Cys Ala Pro Gly Thr Phe Ser Asn Thr Thr Ser
                            260                 265                 270
            Ser Thr Asp Ile Cys Arg Pro His Gln Ile Cys Asn Val Val Ala Ile
                            275                 280                 285
            Pro Gly Asn Ala Ser Met Asp Ala Val Cys Thr Ser Thr Ser Pro Thr
                            290                 295                 300
            Arg Ser Met Ala Pro Gly Ala Val His Leu Pro Gln Pro Val Ser Thr
            305                 310                 315                 320
            Arg Ser Gln His Thr Gln Pro Thr Pro Glu Pro Ser Thr Ala Pro Ser
                            325                 330                 335
            Thr Ser Phe Leu Leu Pro Met Gly Pro Ser Pro Pro Ala Glu Gly Ser
                            340                 345                 350
            Thr Gly Asp Leu Glu Asp Lys Thr His Thr Cys Pro Pro Cys Pro Ala
                            355                 360                 365
            Pro Glu Leu Leu Gly Gly Pro Ser Val Phe Leu Phe Pro Pro Lys Pro
                            370                 375                 380
            Lys Asp Thr Leu Met Ile Ser Arg Thr Pro Glu Val Thr Cys Val Val
            385                 390                 395                 400
            Val Asp Val Ser His Glu Asp Pro Glu Val Lys Phe Asn Trp Tyr Val
                            405                 410                 415
            Asp Gly Val Glu Val His Asn Ala Lys Thr Lys Pro Arg Glu Glu Gln
                            420                 425                 430
            Tyr Asn Ser Thr Tyr Arg Val Val Ser Val Leu Thr Val Leu His Gln
                            435                 440                 445
            Asp Trp Leu Asn Gly Lys Glu Tyr Lys Cys Lys Val Ser Asn Lys Ala
                            450                 455                 460
            Leu Pro Ala Pro Ile Glu Lys Thr Ile Ser Lys Ala Lys Gly Gln Pro
            465                 470                 475                 480
            Arg Glu Pro Gln Val Tyr Thr Leu Pro Pro Ser Arg Glu Glu Met Thr
                            485                 490                 495
            Lys Asn Gln Val Ser Leu Thr Cys Leu Val Lys Gly Phe Tyr Pro Ser
                            500                 505                 510
            Asp Ile Ala Val Glu Trp Glu Ser Asn Gly Gln Pro Glu Asn Asn Tyr
                            515                 520                 525
            Lys Thr Thr Pro Pro Val Leu Asp Ser Asp Gly Ser Phe Phe Leu Tyr
                            530                 535                 540
            Ser Lys Leu Thr Val Asp Lys Ser Arg Trp Gln Gln Gly Asn Val Phe
            545                 550                 555                 560
            Ser Cys Ser Val Met His Glu Ala Leu His Asn His Tyr Thr Gln Lys
                            565                 570                 575
            Ser Leu Ser Leu Ser Pro Gly Lys
                            580
```

FUSION PROTEIN CAPABLE OF BINDING VEGF-A AND TNF-ALPHA

CROSS-REFERENCE TO RELATED APPLICATIONS

The present application claims the benefit of priority to U.S. provisional application No. 61/121,868, filed Dec. 11, 2008, the contents of which are incorporated by reference herein in their entirety.

BACKGROUND OF THE INVENTION

1. Field of the Invention

The present invention relates to a fusion protein capable of synchronously binding vascular endothelial growth factor (VEGF) and tumor necrosis factor alpha (TNF-α), which are referred to herein as "double anti-inflammation-angiogenesis protein targeting both VEGF-A and TNF-alpha, or 'Valpha'". Valpha is disclosed which are therapeutically useful for treating VEGF-A- and TNF-α-associated conditions and diseases such as rheumatoid arthritis, osteoarthritis, psoriasis, diabetic and aged macular degerative retinophaties, cancer, sclerosis, inflammatory bowel disease, polycystic kidney, ankylosing spondylitis, Crohn's disease, ulcerative colitis, and atherosclerosis, and other acute and chronic inflammations.

2. Description of the Background

Vascular endothelial growth factor-A (VEGF-A) plays a crucial role for growth, migration, and survival of blood endothelial cells, which are essential processes for angiogenesis and vasculogenesis mainly through activation of VEGFR1 and VEGFR2 (Ferrara N. et al., Nature Medicine 9:669-676, 2003; Shibuya M and Claesson-Welsh L, Exp. Cell Res. 312:549-560, 2005). VEGF is a prime molecule for tumor angiogenesis and metastasis, abnormal and inflammatory angiogenesis in rheumatoid arthritis, osteoarthritis, psoriasis, diabetic and aged macular degerative retinophaties (Ferrara N. et al., *Nature Medicine* 9:669-676, 2003; DeBandt M. et al., *J Immunol.* 171:4853-4859, 2003; Aiello L P. *N. Engl. J. Med.* 353: 839-841, 2005).

Tumor necrosis factor-alpha (TNF-α) mediates immune response by recruiting leukocyte to the site of inflammation (Hickey M J. et al., *J Immunol* 158: 3391-3400, 1997). TNF-α is a prime molecule in initiating inflammation through activation of NF-κB in the inflammatory cells including macrophages, endothelial cells and dendritic cells (Rojanasakul Y. et al., *Mol. Cell. Biochem.* 200: 119-125, 1999).

Elevated levels of VEGF-A and TNF-α are major determinants in diseases related to inflammatory angiogenesis, such as rheumatoid arthritis, osteoarthritis, psoriasis, diabetic and aged macular degerative retinophaties, cancer, sclerosis, inflammatory bowel disease, polycystic kidney, ankylosing spondylitis, Crohn's disease, ulcerative colitis, and atherosclerosis, and other acute and chronic inflammations. Therefore, simultaneous inhibition of VEGF and TNF-α may be more effective than single inhibition of VEGF or TNF-α in treating these diseases.

SUMMARY OF THE INVENTION

The present invention provides a fusion protein capable of synchronously binding vascular endothelial growth factor (VEGF) and tumor necrosis factor alpha (TNF-α), namely "double anti-inflammation-angiogenesis protein targeting both VEGF-A and TNF-alpha-'Valpha'". Valpha is disclosed which are therapeutically useful for treating VEGF-A- and TNF-α-associated conditions and diseases such as rheumatoid arthritis, osteoarthritis, psoriasis, diabetic and aged macular degerative retinophaties, cancer, sclerosis, inflammatory bowel disease, polycystic kidney, ankylosing spondylitis, Crohn's disease, ulcerative colitis, and atherosclerosis, and other acute and chronic inflammations.

In one aspect, the present invention is directed to an isolated nucleic acid molecule encoding a polypeptide capable of binding VEGF-A and TNF-α polypeptides, which includes a nucleotide sequence encoding a VEGFR1 component and TNFR2 component. A nucleotide sequence encoding a multimerizing component may be linked to a nucleotide sequence encoding a VEGFR1 component and TNFR2 component. And the multimerizing component may be an immunoglobulin domain. In one aspect, the immunoglobulin domain may be the Fc domain of IgG, the heavy chain of IgG, or the light chain of IgG.

In another aspect, in the nucleic acid molecule, the VEGFR1 component and TNFR2 component may include a nucleotide sequence encoding the amino acid sequences of extracellular domains of VEGFR1 and TNFR2.

In another aspect, the invention is directed to an isolated nucleic acid or polypeptide molecule comprising a nucleotide sequence or amino acid sequence as follows:

(a) the nucleotide and amino acid sequence set forth in Table 1 referred to as Valpha FV#1, which includes hTNFR2 signal sequence amino acids from 1 to 22 (nucleotides from 1 to 66), which is taken from amino acids from 1 to 22 (nucleotides from 1 to 66) of the original hTNFR2 construct, hTNFR2 amino acids from 23 to 257 (nucleotides from 67 to 771), which is taken from amino acids from 23 to 257 (nucleotides from 67 to 771) of the original hTNFR2 construct, hVEGFR1 amino acids from 258 to 351 (nucleotides 772 to 1053), which is taken from amino acids from 132 to 225 (nucleotides from 394 to 675) of the original hVEGFR1 construct, and Fc domain of human IgG amino acids from 352 to 581 (nucleotides 1054 to 1743);

(b) the nucleotide and amino acid sequence set forth in Table 2 referred to as Valpha VF#1, which includes hVEGFR1 signal sequence amino acids from 1 to 26 (nucleotides from 1 to 78), which is taken from amino acids 132 to 225 (nucleotides from 394 to 675) of the original hVEGFR1 construct, hVEGFR1 amino acids from 27 to 120 (nucleotides from 79 to 360), which is taken from amino acids from 132 to 225 (nucleotides from 394 to 675) of the original hVEGFR1 construct, hTNFR2 amino acids from 121 to 355 (nucleotides 361 to 1065), which is taken from amino acids from 23 to 257 (nucleotides from 67 to 771) of the original hTNFR2 construct, and Fc domain of human IgG amino acids from 356 to 585 (nucleotides 1066 to 1755); or (c) a nucleotide sequence which, as a result of the degeneracy of the genetic code, differs from the nucleotide sequence of (a) or (b) but which encodes identical amino acid sequence as expressed therefrom.

The invention is also directed to a vector that includes the nucleic acid molecules described above. The vector may be an expression vector.

The invention is also directed to a host-vector system for the production of a fusion polypeptide which includes the expression vector described above in a suitable host cell. Such a suitable host cell may include a bacterial cell, yeast cell, insect cell, or mammalian cell.

The invention is also directed to a fusion polypeptide encoded by any of the isolated nucleic acid molecules described above, including, but not limited to the amino acid sequence for Valpha FV#1 and Valpha VF#1.

The invention is also directed to a composition capable of simultaneously binding VEGF-A and TNF-α molecules to form a nonfunctional complex. The molecule may comprise a multimer of the fusion polypeptide described above including, but not limited to, those fusion constructs that use VEGFR1 and TNFR2 components. In particular, the multimer may be a dimer.

In another aspect, the invention is directed to a method of producing a fusion polypeptide which includes growing cells of the host-vector system described above, under conditions permitting production of the fusion polypeptide and recovering the fusion polypeptide so produced. Such a fusion polypeptide may be modified by acetylation or pegylation. The acetylation may be accomplished with a molar excess of acetylation reagent ranging from at least about a 10 fold molar excess to about a 100 fold molar excess. The pegylation may be with 10K or 20K PEG.

In still another aspect, the invention is directed to a method of decreasing or inhibiting plasma leakage in a mammal, which includes administering to a mammal in need thereof an effective amount of the fusion polypeptide described herein. In a preferred embodiment, the leakage may be in the retina.

In still another aspect, the invention is directed to a method of blocking blood vessel growth in a mammal, which includes administering to a mammal in need thereof an effective amount of the fusion polypeptide described herein. In certain aspects, blood vessel growth blocking activity may be useful for treating cancer, age-related macular degeneration, diabetic retinopathy, rheumatoid arthritis, psoriasis, acute and chronic inflammation, atherosclerosis and lymphatic proliferative diseases, among others.

In still another aspect, the invention is directed to a method of attenuating or preventing tumor growth in a mammal, which includes administering to a mammal in need thereof an effective amount of the fusion polypeptide described herein.

In still another aspect, the invention is directed to a method of attenuating or preventing edema in a mammal, which includes administering to a mammal in need thereof an effective amount of the fusion polypeptide described herein. The edema may be retinal edema or brain edema.

In still another aspect, the invention is directed to a method of attenuating or preventing ascites formation in a mammal, which includes administering to a mammal in need thereof an effective amount of the fusion polypeptide described herein. The ascites may be associated with ovarian cancer. The invention is also directed to a method of inhibiting VEGF receptor ligand and TNF receptor ligand activities in a mammal comprising administering to the mammal an effective amount of the fusion polypeptide described herein.

In still another aspect, the invention is directed to a method of attenuating or preventing inflammatory angiogenesis in a mammal, which includes administering to a mammal in need thereof an effective amount of the fusion polypeptide described herein. An example of a disorder caused by inflammatory angiogenesis is rheumatoid arthritis. Other examples of disorders caused by inflammatory angiogenesis include without limitation, spondyloarthropathies, psoriasis, diabetic retinopathy, atherosclerosis, and sepsis.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1 also shows schematic diagrams of human TNF receptor 1 (TNFR1) or 2 (TNFR2) and their three major regions: an extracellular domain consisting of four cysteine rich domains, a transmembrane domain, and an intracellular domain.

FIGS. 13A-13B show surface plasmon resonance analysis for detection of binding affinity of Valpha between VEGF-A (A) or TNF-α (B). For VEGF-A binding; Valpha has a $K_D$ value of $6.54 \times 10^{-12}$ M, whereas VEGF-Trap has a $K_D$ value of $1.35\times10^{-12}$ M. For TNF-α binding; Valpha has a $K_D$ value of $6.41\times10^{-10}$ M, whereas ENBREL® has a $K_D$ value of $2.29\times10^{-10}$ M.

FIGS. 16A-16B show MTT assay regarding the effect of Valpha in the TNF-α-induced cytotoxicity in L929 murine fibrosarcoma cells. FIG. 16A shows the extent of cell cytotoxicity induced by administration of serially diluted TNF-α (from 10 ng/ml to 0.0005 ng/ml). FIG. 16B shows differential inhibition of Valpha, ENBREL®, Infliximab (REMICADE®), and VEGF-Trap in TNF-α (5 ng/ml)-induced cell toxicities.

FIG. 18 shows a schematic diagram for generation of mice model of retinopathy which is known as retinopathy of prematurity (ROP) or an oxygen-induced retinopathy (OIR) model. Postnatal 7 day (P7) old mice grown in normal atmosphere (normoxia) were transferred and allowed to live in hyperoxic condition (75% $O_2$) for 5 days (P12), and transferred back to normoxic condition, and allowed to live for subsequent 5 days (P17). At P17, profound vascular tufts formation is detected in middle and distal parts of retinal vessels while no vessels are detected in proximal part of retina (vaso-obliteration).

DETAILED DESCRIPTION OF THE INVENTION

Figure 1:
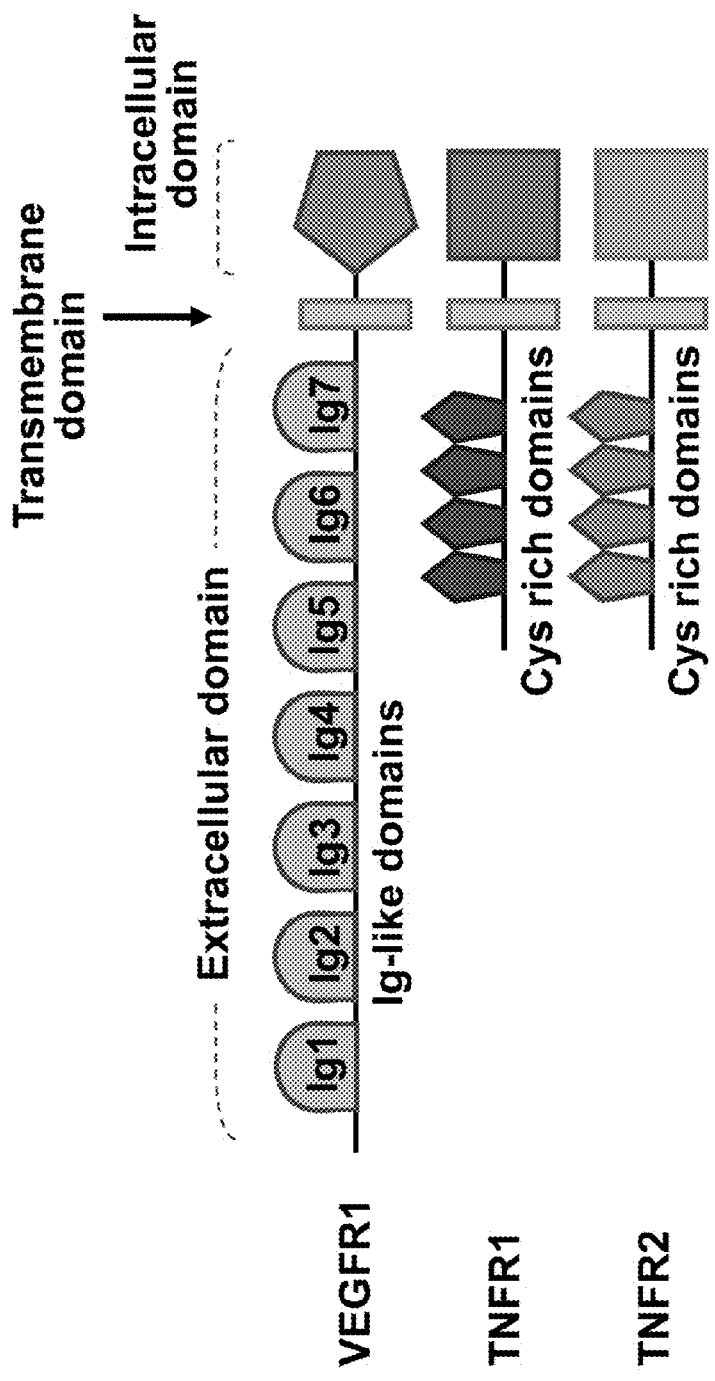
FIG. 1 shows schematic diagram of human VEGFR1 and its three major regions: an extracellular domain consisting of seven immunoglobulin (Ig)-like domains, a transmembrane domain, and an intracellular domain.
Figure 2:
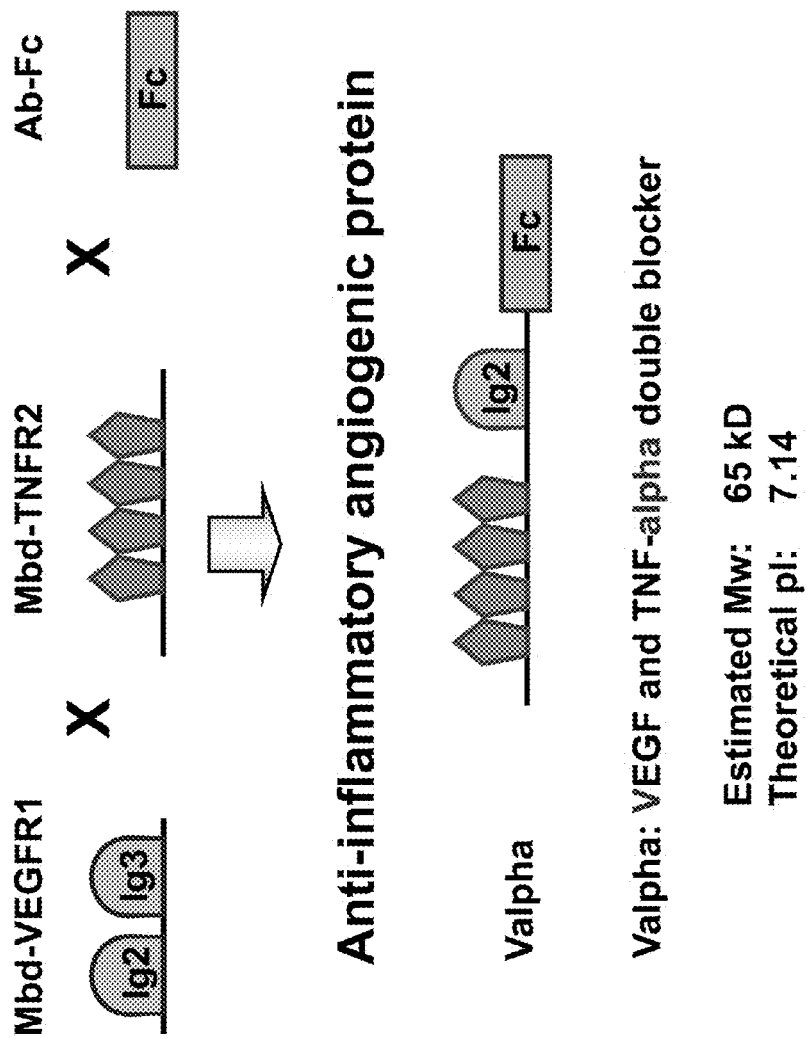
FIG. 2 shows schematic diagrams for making Valpha by combination of the minimum ligand binding domain of VEGFR1 (Mbd-VEGFR1), the minimum ligand binding domain of TNFR2 (Mbd-TNFR2), and Fc portion of human IgG. The four cysteine rich domains of TNFR2 are essential for TNF-α binding, whereas the Ig-like domain 2 (Ig2) of VEGFR1 is essential for VEGF-A binding. Essentially, Mbd-TNFR2 is located in the amino-terminal portion, Ig2 of VEGFR1 is located in middle portion, and Fc portion of human IgG is located in carboxy-terminal portion of Valpha, which is a double blocker of VEGF and TNF-α and acts as anti-inflammatory and anti-angiogenic protein. Estimated molecular weight of Valpha is ~65 kD and theoretical pI value of Valpha is 7.14.

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, "antagonist" refers to a ligand that tends to nullify the action of another ligand, as a ligand that binds to a cell receptor without eliciting a biological response.

Preferred biological activities of the ligands of the present invention include the ability to inhibit vascular permeability and the ability to attenuate inflammation. The ability to inhibit vascular permeability will be useful for treatment of medical conditions and diseases such as diabetic retinopathy, edema, and ascites. Preferred biological activities of the ligands of the present invention include the ability to maintain endothelial cell integrity (including preventing apoptosis).

The ability to attenuate inflammation will be useful for treatment of medical conditions and diseases such as rheumatoid arthritis, osteoarthritis, psoriasis, inflammatory bowel disease, ankylosing spondylitis, Crohn's disease, and ulcerative colitis.

It is also contemplated that fusion proteins be labeled with a detectable label, such as radioisotope, fluorescent tag, enzymatic tag, or a chemiluminescent tag to determine ligand-receptor binding interaction. As such, assay systems employing the chimeric molecule is also contemplated.

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "consisting essentially of" when used in the context of a nucleic acid sequence refers to the sequence that is essential to carry out the intended function of the amino acid encoded by the nucleic acid.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

As used herein, "fragments" or "functional derivatives" refers to biologically active amino acid sequence variants and fragments of the native ligands or receptors of the present invention, as well as covalent modifications, including derivatives obtained by reaction with organic derivatizing agents, post-translational modifications, derivatives with nonproteinaceous polymers, and immunoadhesins.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity, such as in a ligand trap.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein "pharmaceutically acceptable carrier and/ or diluent" includes any and all solvents, dispersion media, coatings antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

As used herein, "sample" or "biological sample" is referred to in its broadest sense, and includes any biological sample obtained from an individual, body fluid, cell line, tissue culture, or other source which may contain any TNF-α or VEGF-A binding peptides, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art.

As used herein, "subject" is a vertebrate, preferably a mammal, more preferably a human.

As used herein, "synchronous" or "synchronously" binding refers to the binding of the protein to two or more designated proteins simultaneously if the proteins are available for binding.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

Sequence Listing Free Text

As regards the use of nucleotide symbols other than a, g, c, t, they follow the convention set forth in WIPO Standard ST.25, Appendix 2, Table 1, wherein k represents t or g; n represents a, c, t or g; m represents a or c; r represents a or g; s represents c or g; w represents a or t and y represents c or t.

Table 1 shows SEQ ID NO:1 nucleic acid sequence and its corresponding amino acid sequence (SEQ ID NO:2) for subdomain assemblies of Valpha FV#1 composed of Mbd-TNFR2, Ig2 of VEGFR1, and human IgG Fc portion in order.

The nucleotide and amino acid sequence set forth in Table 1 referred to as Valpha FV#1, which includes hTNFR2 signal sequence amino acids from 1 to 22 (nucleotides from 1 to 66), which is taken from amino acids from 1 to 22 (nucleotides from 1 to 66) of the original hTNFR2 construct, hTNFR2 amino acids from 23 to 257 (nucleotides from 67 to 771), which is taken from amino acids from 23 to 257 (nucleotides from 67 to 771) of the original hTNFR2 construct, hVEGFR1 amino acids from 258 to 351 (nucleotides 772 to 1053), which is taken from amino acids from 132 to 225 (nucleotides from 394 to 675) of the original hVEGFR1 construct, and Fc domain of human IgG amino acids from 352 to 581 (nucleotides 1054 to 1743).

Table 2 shows SEQ ID NO:3 nucleic acid sequence and its corresponding amino acid sequence (SEQ ID NO:4) for subdomain assemblies of Valpha VF#1 composed of Ig2 of VEGFR1, Mbd-TNFR2, and human IgG Fc portion in order.

The nucleotide and amino acid sequence set forth in Table 2 referred to as Valpha VF#1, which includes hVEGFR1 signal sequence amino acids from 1 to 26 (nucleotides from 1 to 78), which is taken from amino acids 132 to 225 (nucleotides from 394 to 675) of the original hVEGFR1 construct, hVEGFR1 amino acids from 27 to 120 (nucleotides from 79 to 360), which is taken from amino acids from 132 to 225 (nucleotides from 394 to 675) of the original hVEGFR1 construct, hTNFR2 amino acids from 121 to 355 (nucleotides 361 to 1065), which is taken from amino acids from 23 to 257 (nucleotides from 67 to 771) of the original hTNFR2 construct, and Fc domain of human IgG amino acids from 356 to 585 (nucleotides 1066 to 1755).

Tables 1 and 2 show the TNFR-Cys domains 1, 2, 3, and 4 and the hVEGFR1 Ig domain 2. Each of these domains may be used separately or mixed and matched according to the present invention. For instance, not all of the domains need to be used together. TNFR-Cys domain 1, 2, 3, or 4 may be used individually or in combination and in conjunction with a domain of hVEGFR1 in order to provide a desired simulataneously binding effect.

Human VEGFR1 and Human TNFR2

Human VEGFR1 is composed of 1338 amino acids, separated by three major regions: an extracellular domain having seven immunoglobulin (Ig)-like domains, a transmembrane domain, and an intracellular tyrosine kinase domain (UniProtKB/Swiss-Prot entry P17948) (FIG. 1). Since VEGFR1 is a well-known protein, its sequence is believed to be not in dispute.

The Ig-like domain 2 among seven Ig-like domains in VEGFR1 is essential for VEGF-A binding (FIG. 2). However, the Ig-like domain 2 of VEGFR1 contains many basic amino acids and its theoretical isoelectric point (pI) is 9.19 (Compute pI/Mw tool for Swiss-Prot/TrEMBL entries, http://kr.expasy.org/tools/pi_tool.html).

In general, positively charged (that is, high value of pI) proteins bind non-specifically to extracellular matrix that is negatively charged. Therefore, the Ig-like domain 2 of VEGFR1 per se may not be useful as a therapeutic protein because it may have poor pharmacokinetic properties.

There are two known TNF receptors, TNFR1 (molecular weight, 55 kD; TNF-R55) and TNFR2 (molecular weight, 75 kD; TNF-R75) (FIG. 1). These two receptors have similar affinities for TNF-α and TNF-β (Schall et al., Cell 1990, 61:361-370). The affinity of TNF-α to TNFR2 is several times higher than that to TNFR1 (Dri P. et al., *J Immunol* 162:460-466, 1999; Tartaglia L A. et al., *J. Biol. Chem.* 268: 18542-18548, 1993). Since TNFR1 and TNFR2 are well-known proteins, it is believed that their sequences are not in dispute.

Human TNFR2 includes 461 amino acids, separated by three major regions: an extracellular domain consisting of four cysteine rich domains, a transmembrane domain, and an intracellular domain (UniProtKB/Swiss-Prot entry P20333) (FIG. 1).

The four cysteine rich domains of extracellular subdomain of TNFR2 are essential for TNF binding (FIG. 2). Although this subdomain contains many basic amino acids, its theoretical isoelectric point (pI) is 6.5 (Compute pI/Mw tool for Swiss-Prot/TrEMBL entries, http://kr.expasy.org/tools/pi_tool.html) because it possesses high amounts of cysteines and other acidic amino acids.

VEGF superfamily includes VEGF-A, -B, -C, -D, and PlGF, whereas TNF superfamily consists of TNF-α (cachectin) and TNF-β (lymphotoxin). Among them, VEGF-A and TNF-α are critical molecules for pathological inflammation and angiogenesis. The present invention provides synchronous blockade of VEGF-A and TNF-α, preferably with a decoy receptor, intradiabody (double antibody), or RNA interference for treating VEGF-A and/or TNF-associated diseases.

Nucleic Acid Constructs

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS or CHO cell.

The present invention also provides for methods of producing the fusion polypeptides of the invention by growing cells of the host-vector system described herein, under conditions permitting production of the fusion polypeptide and recovering the fusion polypeptide so produced. The fusion polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, fusion polypeptide includes functionally equivalent molecules in which amino acid residues are substituted for residues within the sequence resulting in a silent or conservative change. For example, one or more amino acid residues within the sequence can be substituted by another amino acid of a similar polarity which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the fusion polypeptides of the invention are genetically engineered to produce them by, for example, transfection, transduction, electroporation, or microinjection techniques.

In addition, the present invention contemplates use of the fusion polypeptides described herein in tagged form.

Any of the methods known to one skilled in the art for the insertion of DNA fragments into a vector may be used to construct expression vectors encoding the fusion polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the fusion polypeptides of the invention may be regulated by a second nucleic acid sequence so that the fusion polypeptide is expressed in a host transformed with the recombinant DNA molecule. For example, expression of the fusion polypeptides described herein may be controlled by any promoter/enhancer element known in the art. Promoters which may be used to control expression of the fusion polypeptide include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235: 53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a fusion polypeptide as described herein, and in particular modified, are used to transfect the host and thereby direct expression of such nucleic acid to produce fusion polypeptides which may then be recovered in biologically active form. As used herein, a biologically active form includes a form capable of binding to the relevant receptor and causing a differentiated function and/or influencing the phenotype of the cell expressing the receptor. Such biologically active forms would, for example, block phosphorylations of the VEGFR1, VEGFR2 and TNFR2 receptors, or inhibiting of synthesis of cellular DNA.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The fusion polypeptide, in particular modified of the present invention, may be expressed in the host cells transiently, constitutively or permanently.

The invention herein further provides for the development of a fusion polypeptide as a therapeutic agent for the treatment of patients suffering from disorders involving cells, tissues or organs which express the VEGFR-1, VEGFR-2 and TNFR-2 receptors. Such molecules may be used in a method of treatment of the human or animal body, or in a method of diagnosis.

Effective doses useful for treating these or other diseases or disorders may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the fusion polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a fusion polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the fusion polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

In a specific embodiment, nucleic acids comprising sequences encoding the chimeric TNF-α polypeptide are administered to prevent vascular leakage, and for therapeutic vasculogenesis, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a chimeric-TNF-α or TNFR2 polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

In one embodiment, the present invention relates to treatment for various diseases that are characterized by vascular leakage or lack of blood vessel formation. In this way, the inventive therapeutic compound may be administered to human patients who are either suffering from, or prone to suffer from the disease by providing compounds that activate TNFR-2, VEGFR-2 and VEGFR-1.

The formulation of therapeutic compounds is generally known in the art and reference can conveniently be made to Remington's Pharmaceutical Sciences, 17th ed., Mack Publishing Co., Easton, Pa., USA. For example, from about 0.05 ng to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the chimeric-TNF-α, TNFR-2 or chimeric TNF-α/TNFR-2 complex-specific antibodies of the present invention are provided below. Examples of suitable enzyme labels include malate dehydrogenase, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is preferred isotope where in vivo imaging is used since its avoids the problem of dehalogenation of the $^{125}$I or $^{131}$I-labeled polypeptide by the liver. In addition, this radionucleotide has a more favorable gamma emission energy for imaging. For example, $^{111}$In coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Typical techniques for binding the above-described labels to polypeptides are provided by Kennedy et al. (Clin. Chim. Acta 70:1-31 1976 and Schurs et al. Clin. Chim. Acta 81:1-40, 1977). Coupling techniques include the glutaraldehyde method, the periodate method, the dimaleimide method, the m-maleimidobenzyl-N-hydroxy-succinimide ester method, all of which methods are incorporated by reference herein.

The polypeptides and antibodies of the present invention, including fragments thereof, may be used to detect chimeric-TNF-α, TNFR-2 or chimeric TNF-α/TNFR-2 complex using biochip and biosensor technology. Biochip and biosensors of the present invention may comprise the polypeptides of the present invention to detect antibodies, which specifically recognize chimeric TNF-α/TNFR-2 complex. Bio chip and biosensors of the present invention may also comprise antibodies which specifically recognize the polypeptides of the present invention to detect chimeric TNF-α/TNFR-2 complex.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Gene Construction and Expression of Recombinant Valpha Protein

Figure 3:
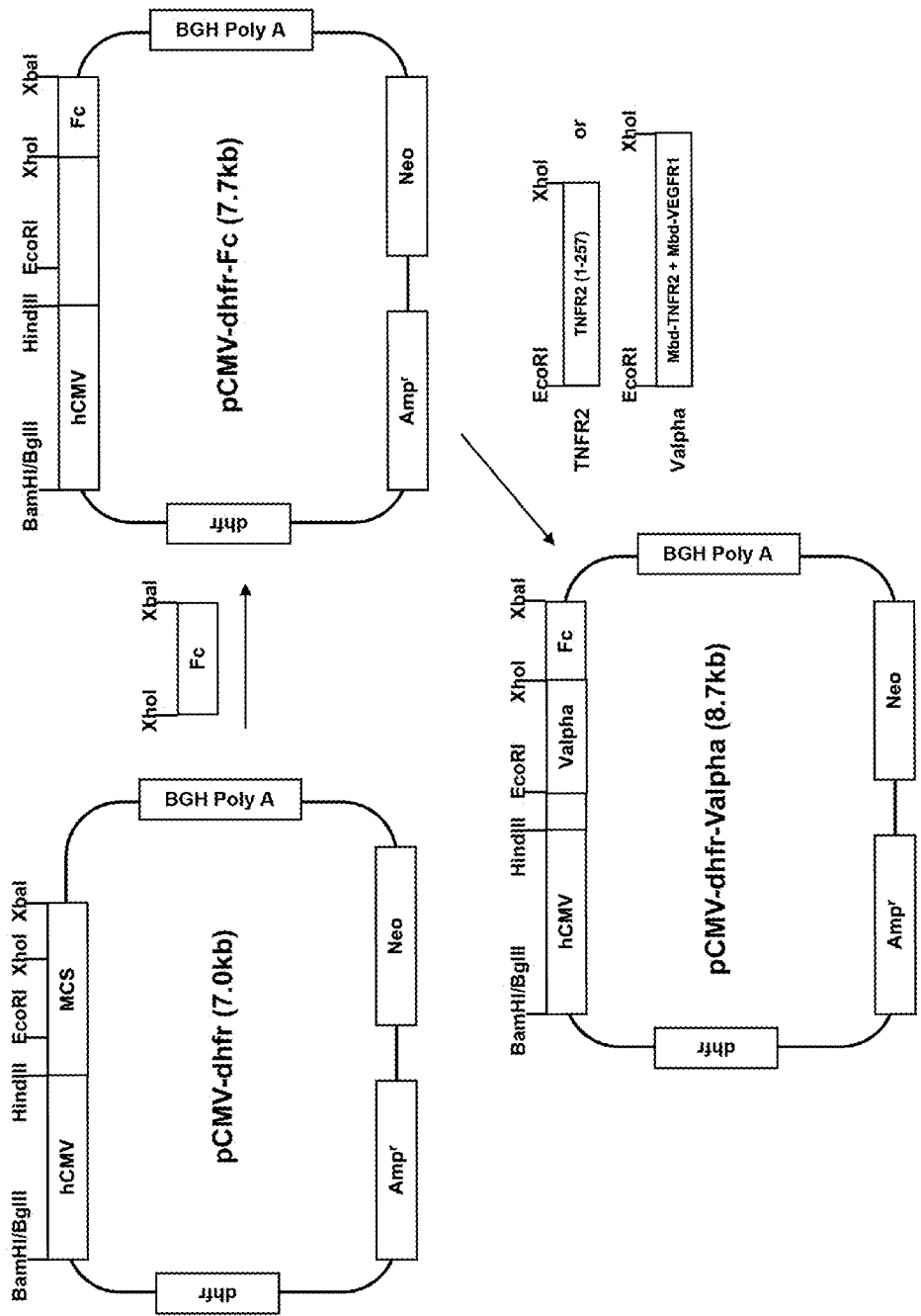
FIG. 3 shows schematic diagrams of gene constructs, pCMV-dhfr, pCMV-dhfr-Fc, pCMV-dhfr-Valpha, for Valpha protein expression using mammalian cell culture system. After insertion of the gene encoding Fc of human IgG for subdomain into pCMV-dhfr, the gene encoding Valpha was inserted into pCMV-dhfr-Fc. Standard molecular methods were used to generate pCMV-dhfr-Valpha gene construct. EcoRI and XhoI are major restriction enzyme sites.

Gene constructs encoding a fusion protein 'Valpha' (FIG. 3) that includes cysteine rich domains of human TNFR2, Ig-like domain of human VEGFR1 and Fc domain of human IgG were cloned into the pCMV-dhfr vector (Hwang S J, et al., Protein Express Purif. 2005; 39:175-183).

Figure 4:
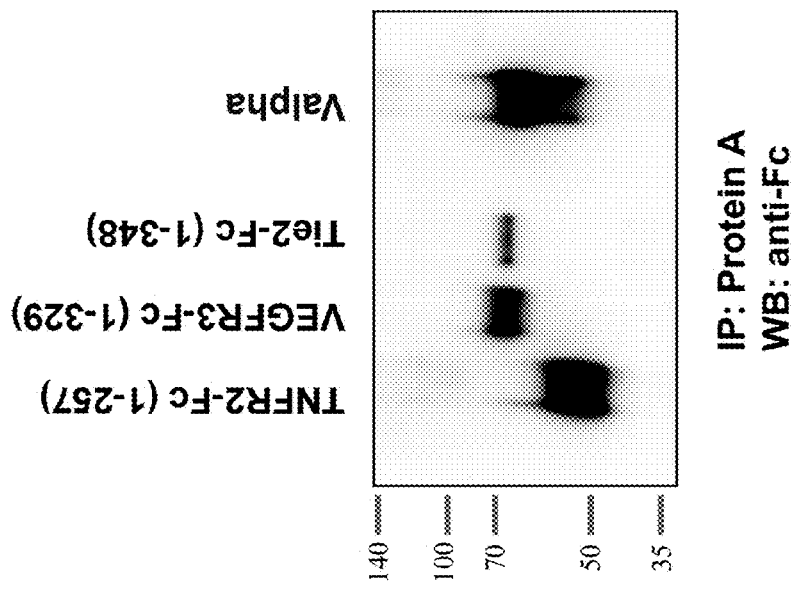
FIG. 4 shows Western blot analysis for TNFR2-Fc, VEGFR3-Fc, Tie2-Fc, and Valpha proteins produced as transiently expressed in HEK293 cell. Expression and secretion levels for TNFR2-Fc (1-257) and Valpha were higher than those for VEGFR3-Fc (1-329) and Tie2-Fc (1-348).

The protein levels of the recombinant proteins, Valpha, TNFR2-Fc, VEGFR3-Fc and Tie2-Fc were compared by Western blot analysis (FIG. 4). Human embryonic kidney 293 (HEK293) cells (American Type Culture Collection) were transfected with the CMV promoter driven constructs encoding Valpha, TNFR2-Fc, VEGFR3-Fc, or Tie2-Fc using an Effectene liposomal transfection according to the manufacturer's instructions (Qiagen, Inc.). The supernatants were harvested from transfected cells at 48 hour after transfection. The recombinant proteins were immunoprecipitated in 1 ml supernatant by addition of 20 µl of Protein-A sepharose bead, and then washed twice with 1 ml of PBS. Each sample was mixed with sample buffer, heat-denatured for 10 min, and run on 10% SDS-PAGE gel, and electro-blotted onto nitrocellulose membranes. The membrane was blocked with 5% nonfat milk in Tris-buffer solution (50 mM Tris, 100 mM NaCl, pH 7.5) containing 0.05% Triton X-100 and Western blotted with horseradish-peroxidase (HRP)-conjugated goat anti-human Fc antibody (1:10,000 dilution; Sigma-Aldrich A0170) to detect Fc-fused proteins. Signal was visualized by chemiluminescent detection according to the manufacturer's protocol (Amersham Pharmacia Biotech) using chemiluminescence scanner (LAS-1000, Fuji Film, Tokyo) (FIG. 4).

Example 2

Figure 5:
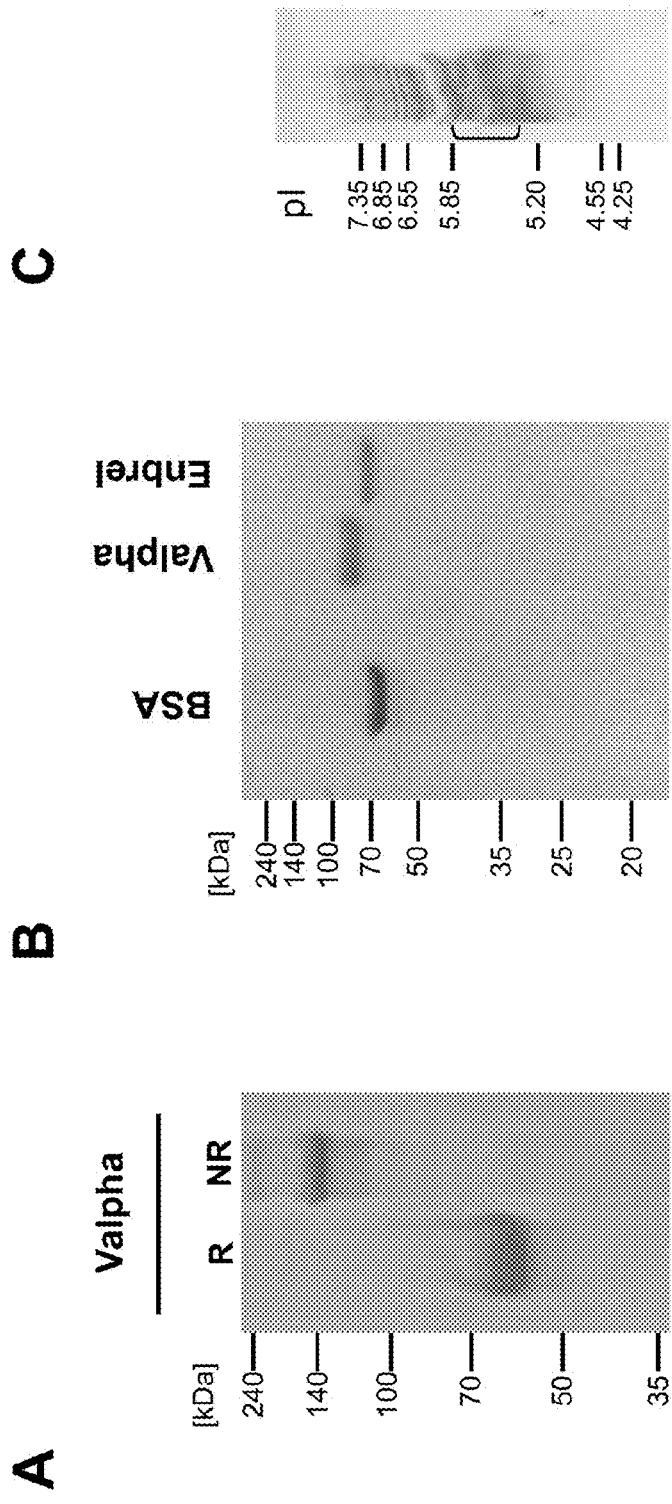
FIGS. 5A-5C show Coomassie staining of SDS-PAGE gels for purified Valpha protein under reducing and non-reducing condition (A), and BSA (bovine serum albumin), Valpha, and ENBREL® (Etanercept) under reducing condition (B), and isoelectric focusing of Valpha (C).

Mass Production of Valpha Protein Using CHO Cells and Isoelectric Focusing of the Valpha Protein Recombinant Chinese hamster ovary (rCHO) cells expressing Valpha ("CHO-Val") was established following a previously described method (Hwang S J. et al., Protein Express Purif. 39:175-183; 2005). Briefly, CHO-Val cells were established by transfection of a vector containing the dihydrofolate reductase (dhfr) and Valpha genes into dhfr-deficient CHO cells (CRL-9096, American Type Culture Collection, Manassas, Va., USA). This was followed by dhfr/methotrexate (MTX)-mediated gene amplification. The three stable rCHO cells secreting Valpha were selected with serial amplified concentrations of MTX (20-320 nM, Sigma-Aldrich). Among them, one cell line expressing the highest amount of Valpha was chosen and named as "CHO-Val". CHO-Val cells were grown and maintained in Iscove's modified Dulbecco's medium supplemented with 5% dialyzed fetal bovine serum (Invitrogen, Carlsbad, Calif., USA) and 20 nM MTX (Sigma-Aldrich). For recombinant Valpha protein production, CHO-Val cells were inoculated at $2 \times 10^5$ cells/mL in 250-ml Erlenmeyer flasks containing 100 ml of medium on an orbital shaker (Vision, Bucheon, Korea) at 110 rpm in a humidified 5% $CO_2$ incubator at 37° C. After indicated days, Valpha recombinant protein was purified by using Protein-A sepharose affinity chromatography, acid elution and subsequent neutralization. After purification, the protein was quantitated using the Bradford assay and confirmed with Coomassie blue staining of an SDS-PAGE gel (FIG. 5A and FIG. 5B). The analysis showed that approximately 20 mg/L of Valpha was harvested from "CHO-Val". Recombinant Valpha protein migrated at ~65 kD under reducing condition and ~130 kD under non-reducing condition (FIG. 5A).

20 µg of Valpha protein was loaded on an IsoGel Agarose IEF Plate pH 3-10 strip (Cambrex) and run at 50 mA constant current for 3 hr using 1M phosphoric acid at the anode and 1M sodium hydroxide at the cathode (FIG. 5C). The gels were stained with Coomassie blue (FIG. 5C).

Example 3

In vitro Binding Capability of the Valpha Protein

Figure 6:
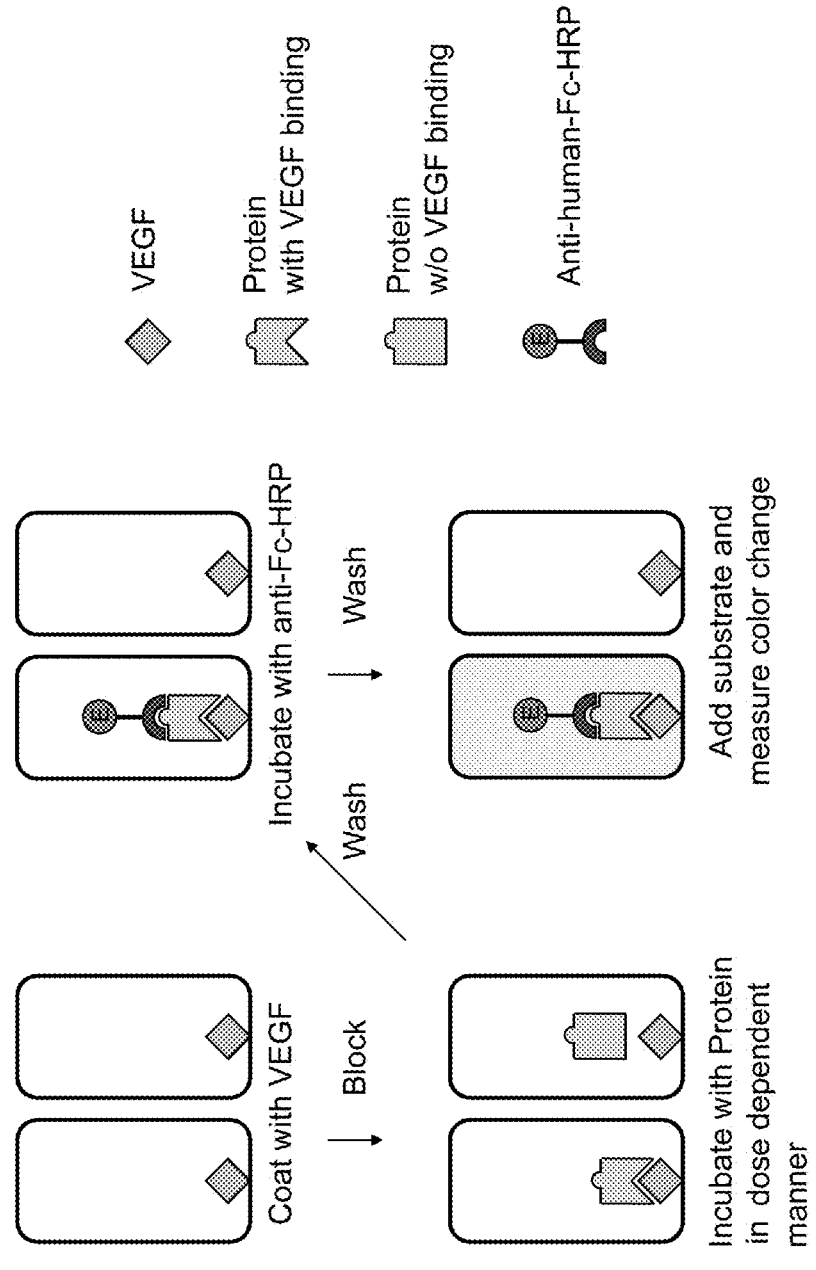
FIG. 6 shows a schematic diagram of a binding assay for Valpha to VEGF-A based on established ELISA method.
Figure 7:
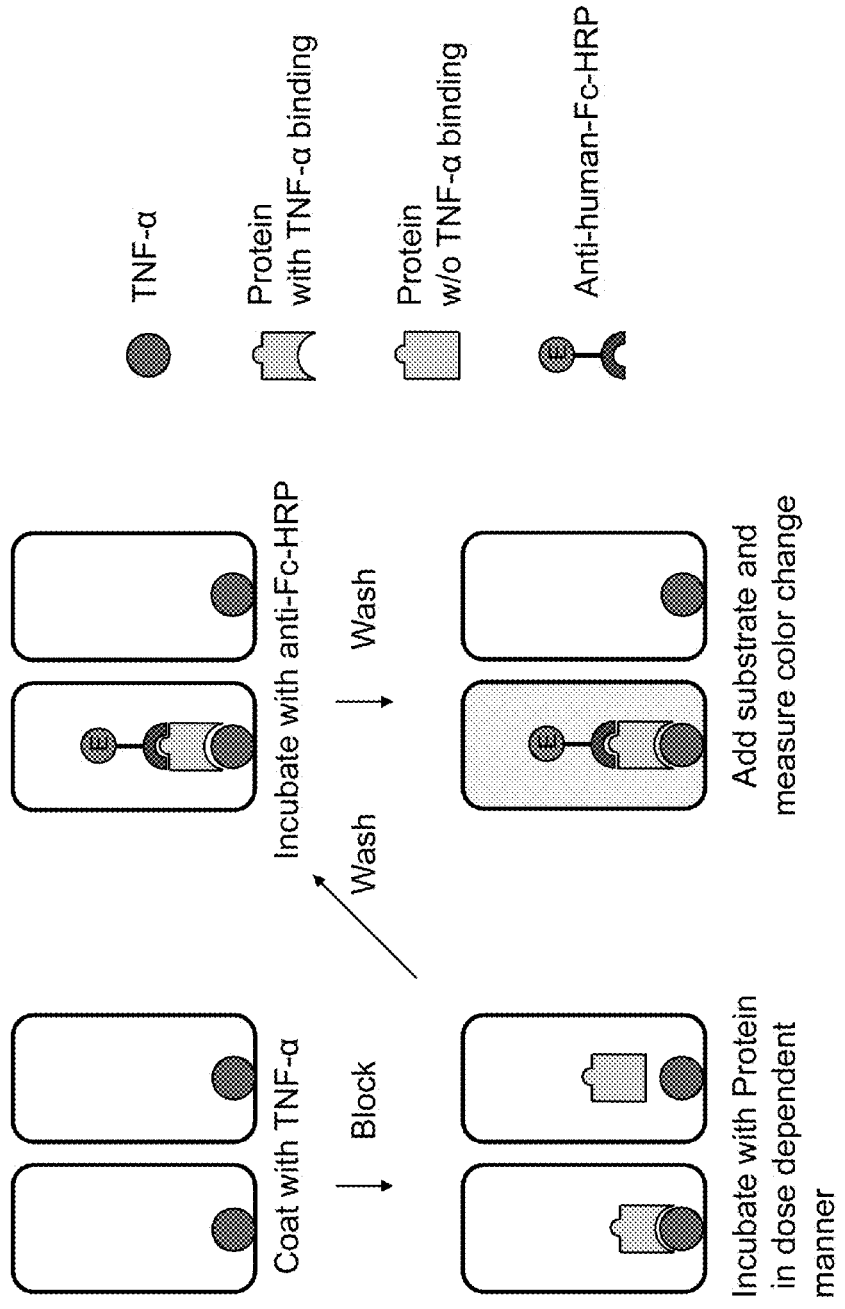
FIG. 7 shows a schematic diagram of a binding assay for Valpha to TNF-α based on established ELISA method.
Figure 8:
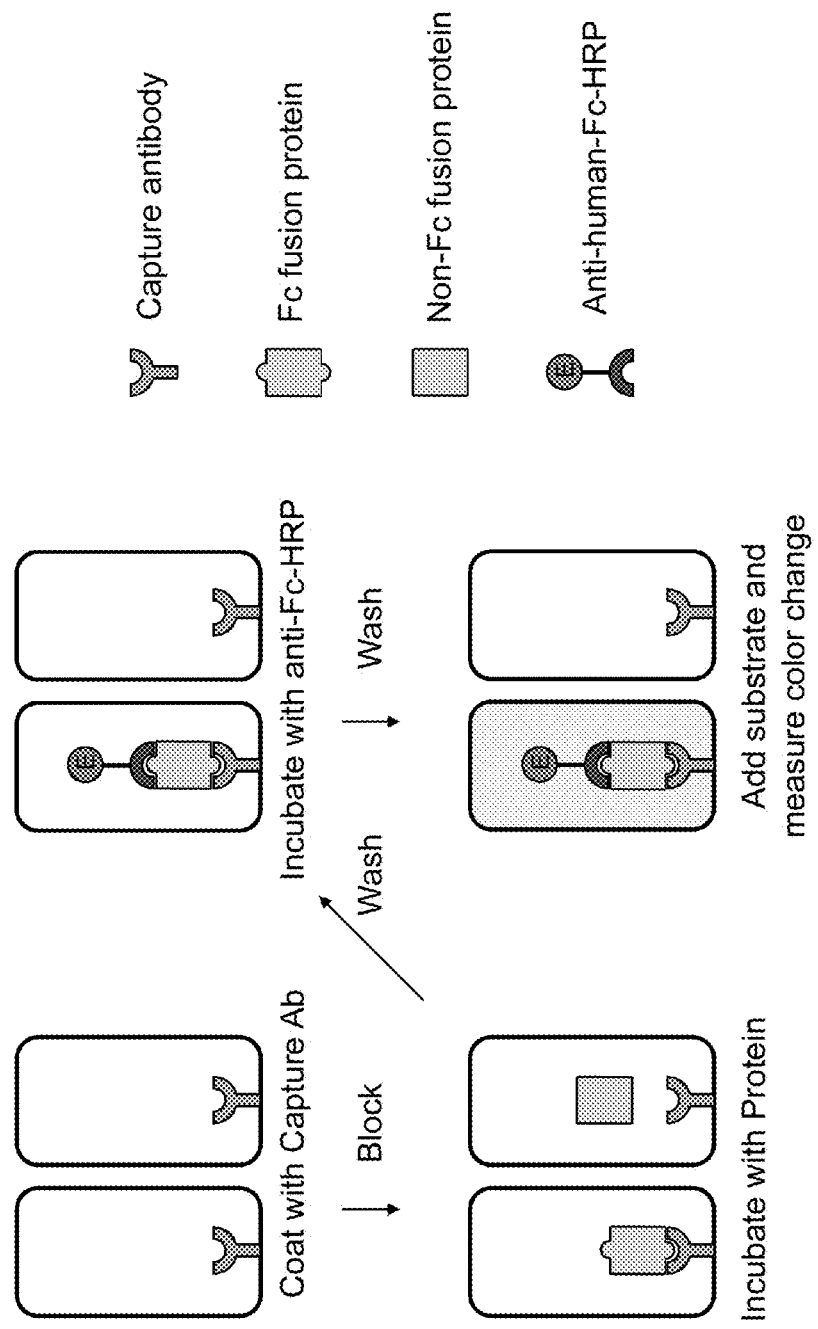
FIG. 8 shows a schematic diagram of a binding assay for detection of Fc fusion protein using a standard ELISA method.

Binding capability of Valpha recombinant protein to VEGF-A or TNF-α was measured by the enzyme-linked immunosorbent assay (ELISA) (FIG. 6 and FIG. 7). Two hundred nanograms of VEGF-$A_{165}$ (produced from CHO cell) (hereafter referred to as VEGF-A), TNF-α (R&D Cat#210-TA/CF), or anti-hIgG Fc specific antibody (Abcam Cat# AB1927) in 100 µl of phosphate buffered saline (PBS) was aliquoted into 96-well plate and incubated at 4° C. for overnight. All Fc fusion proteins were normalized using Fc detection ELISA method (FIG. 8) before VEGF-A or TNF-α binding ELISA. After washing the plate 3 times with each 400

µl of PBS, a blocking was performed with the blocking solution (1% BSA in 100 µl PBS) at 37° C. for 2 hour. Each Fc fusion protein such as Valpha, TNFR2-Fc (also known as Etarnercept, U.S. Pat. No. 5,447,851), VEGF-Trap (Holash J. et al., *Proc. Natl. Acad. Sci. U.S.A* 99:11393-11398, 2002; Jeon B H. et al., *Cancer Research* 68:1100-1109, 2008) in 100 µl of blocking solution was added into the plate, and then were incubated at 37° C. for 2 hour. After washing the plate 3 times with each 400 µl of PBS, 50 µl of horseradish-peroxidase (HRP)-conjugated goat anti-human Fc antibody (1:10,000 dilution; Sigma-Aldrich A0170) was added into the plate, and were incubated at 37° C. for 2 hour. After washing the plate 3 times with each 400 µl of PBS, 50 µl of 3,3',5,5'-tetramethylbenzidine (TMB) solution (Sigma-Aldrich T0440) was added into the plate, and were incubated at room temperature for 10 min. Reaction was stopped by adding 50 µl of 1 M HCl and reactive colors were analyzed at optical density 415 nm by ELISA reader (BioRad M680).

Figure 9:
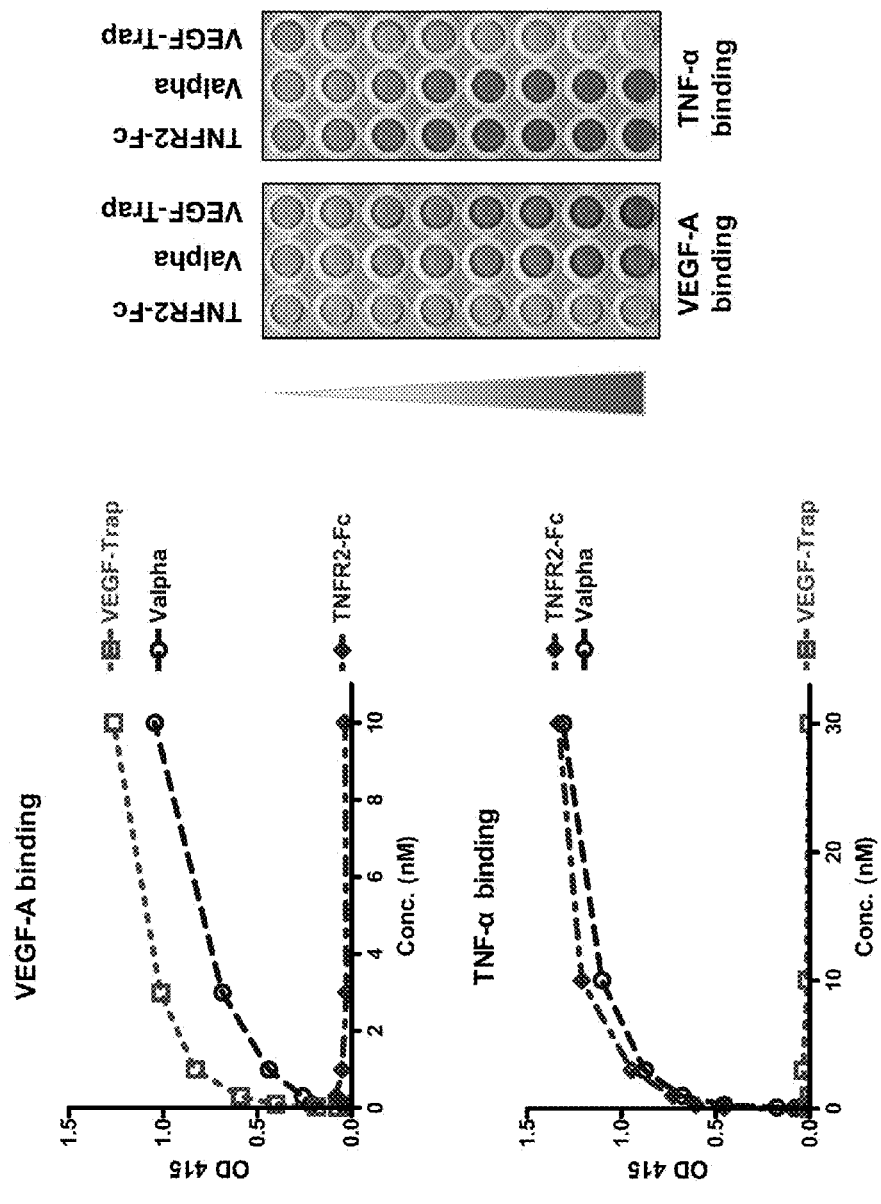
FIG. 9 shows an in vitro binding assay of Valpha to VEGF-A and TNF-α. VEGF-A or TNF-α coated plates were incubated with 0.01~10 nM of Valpha, VEGF-Trap, and TNFR2-Fc for VEGF-A binding or 0.03~30 nM for TNF-α binding. VEGF-Trap and Valpha displayed VEGF-A binding whereas TNFR2-Fc and Valpha displayed TNF-α binding. Binding affinity of Valpha to VEGF-A is slightly weaker than that of VEGF-Trap, whereas binding affinity of Valpha to TNF-α is similar to that of TNFR2-Fc.

The ELISA analyses indicated that Valpha and VEGF-Trap were capable of binding to VEGF-A, whereas Valpha and TNFR2-Fc were capable of binding to TNF-α (FIG. 9). For instance, Valpha is capable of synchronous binding to VEGF-A and TNF-α (FIG. 10 and FIG. 11).

Example 4

In vitro Synchronous Binding to VEGF-A and TNF-α of the Valpha Protein

Figure 10:
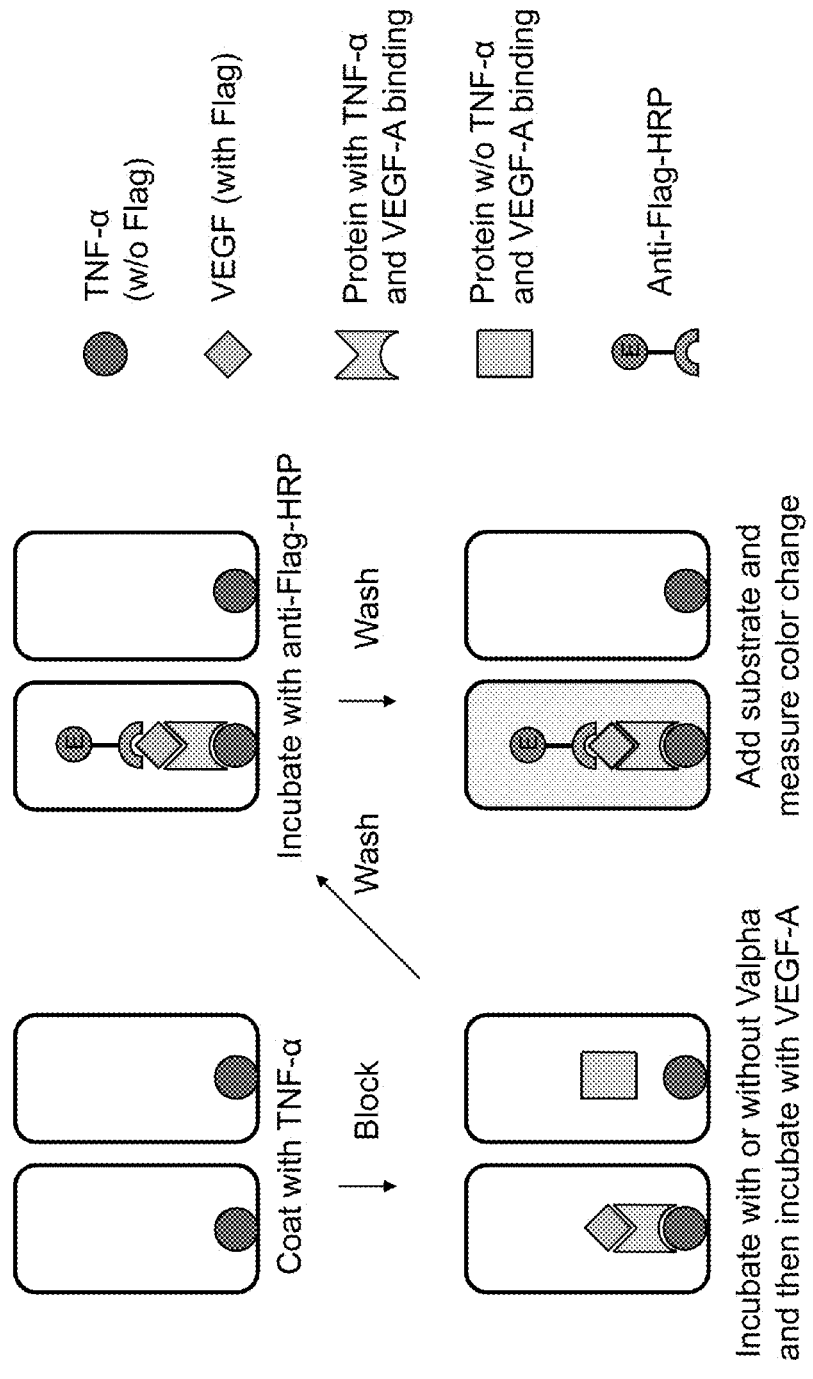
FIG. 10 shows a schematic diagram of an advanced sandwich ELISA binding assay for validation of synchronous binding of Valpha to VEGF-A and TNF-α.
Figure 11:
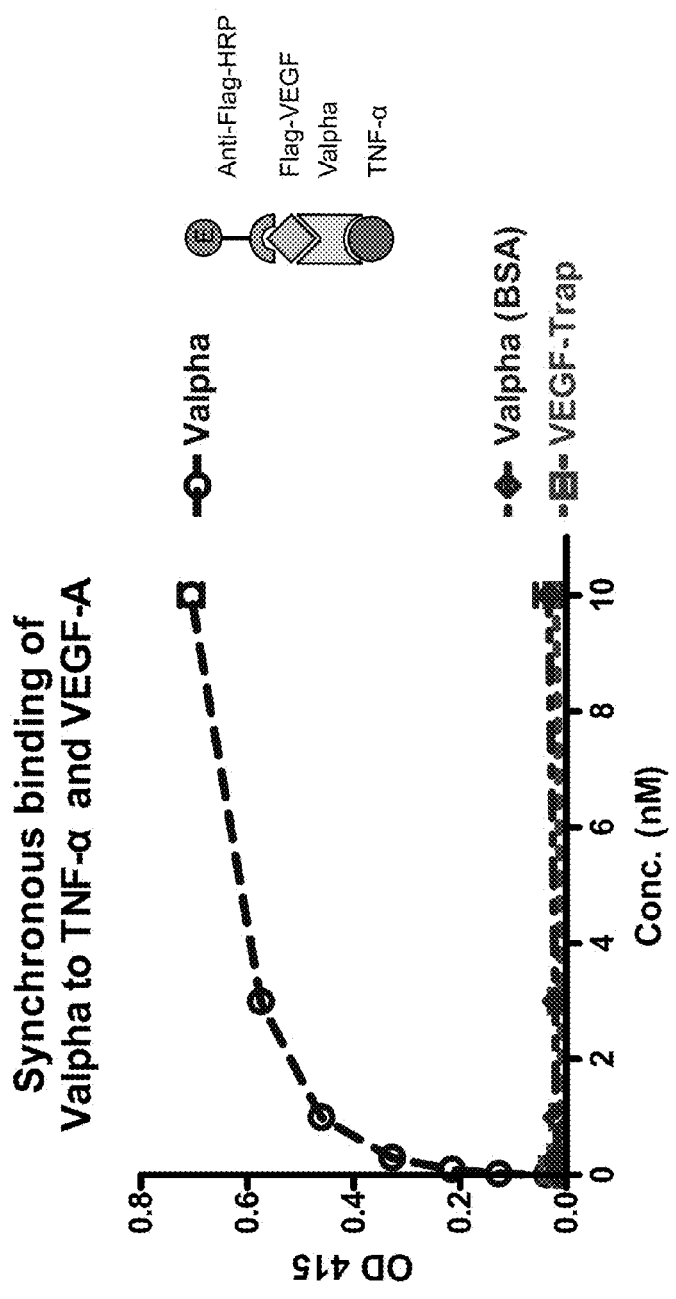
FIG. 11 shows the results the advanced sandwich ELISA assay, which indicate synchronous binding of Valpha to VEGF and TNF-α.

To examine whether Valpha recombinant protein is capable of synchronous binding to VEGF and TNF-α, a new ELISA method was designed (FIG. 10). Two hundred nanograms of TNF-α (R&D Cat#210-TA/CF) or BSA (negative control) in 100 µl of PBS was aliquoted into 96-well plate and incubated at 4° C. for overnight. After washing the plate 3 times with each 400 µl of PBS, a blocking was performed with the blocking solution (1% BSA in 100 µl PBS) at 37° C. for 2 hour. Each Fc fusion protein such as Valpha, TNFR2-Fc, VEGF-Trap in 100 µl of blocking solution was added into the plate, and were incubated at 37° C. for 2 hour. After washing the plate 3 times with each 400 µl of PBS, 1 ng/ml of VEGF-A in blocking solution was added, which has FLAG tag in its amino-terminus. After washing the plate 3 times with each 400 µl of PBS, 50 µl of horseradish-peroxidase (HRP)-conjugated anti-Flag M2 antibody (1:10,000 dilution; Sigma-Aldrich A8592) was added into the plate, and were incubated at 37° C. for 2 hour. After washing the plate 3 times with each 400 µl of PBS, 50 µl of 3,3',5,5'-tetramethylbenzidine (TMB) solution (Sigma-Aldrich T0440) was added into the plate, and were incubated at room temperature for 10 min. Reaction was stopped by adding 50 µl of 1 M HCl and reactive colors were analyzed at optical density 415 nm by ELISA reader (BioRad M680) (FIG. 10).

The optical signals were increased in a dose dependant manner only when Valpha was incubated with TNF-α coating, whereas VEGF-Trap incubated with TNF-α coating or Valpha incubated BSA coating did not change any optical signals (FIG. 11). These results indicated that Valpha recombinant protein captured by TNF-α protein that was immobilized on the plate could bind to soluble FLAG-tagged VEGF-A.

Figure 12:
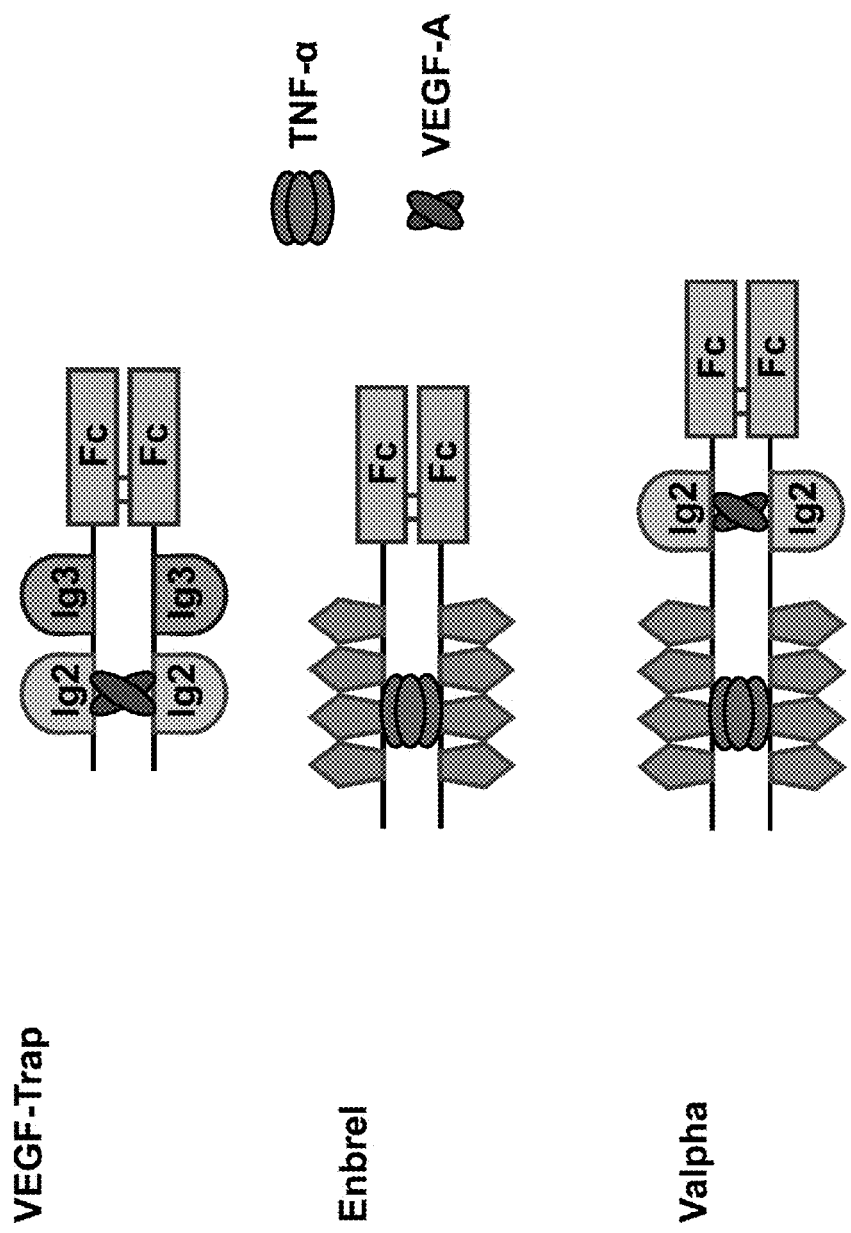
FIG. 12 shows a schematic diagram for binding models of VEGF-Trap, ENBREL®, and Valpha to VEGF and TNF-α.

These results indicate that Valpha recombinant protein is capable of simultaneous binding to VEGF-A and TNF-α, whereas VEGF-Trap is capable of binding to VEGF-A only and ENBREL® (TNFR2-Fc) is capable of binding to TNF-α only (FIG. 12).

Example 5

Analysis of the Interaction Between Valpha and VEGF-A or TNF-α

Binding between Valpha and VEGF-A or TNF-α were analyzed with the BIAcore 3000 (BIAcore AB). One microgram of VEGF-A or TNF-α was immobilized on a Sensor Chip CM5 (BIAcore) using N-hydroxysuccinimide (NHS) and 1-ethyl-3(3-dimethylaminopropyl) carbodiimide (EDC) amine coupling reagent at approximately 2,000 resonance units (RU). As a control, BSA protein was immobilized on another portion of the same chip. Recombinant Valpha, VEGF-Trap, or ENBREL® proteins were then applied onto the immobilized VEGF-A or TNF-α surfaces, and the amount captured was recorded in sensorgrams as RU (FIG. 13). All samples were in running buffer to minimize bulk effects. The kinetic parameters of the binding interactions were calculated from the sensorgrams by nonlinear curve fitting using BIAEVALUATION software (BIAcore) (FIG. 13).

Example 6

Figure 14:
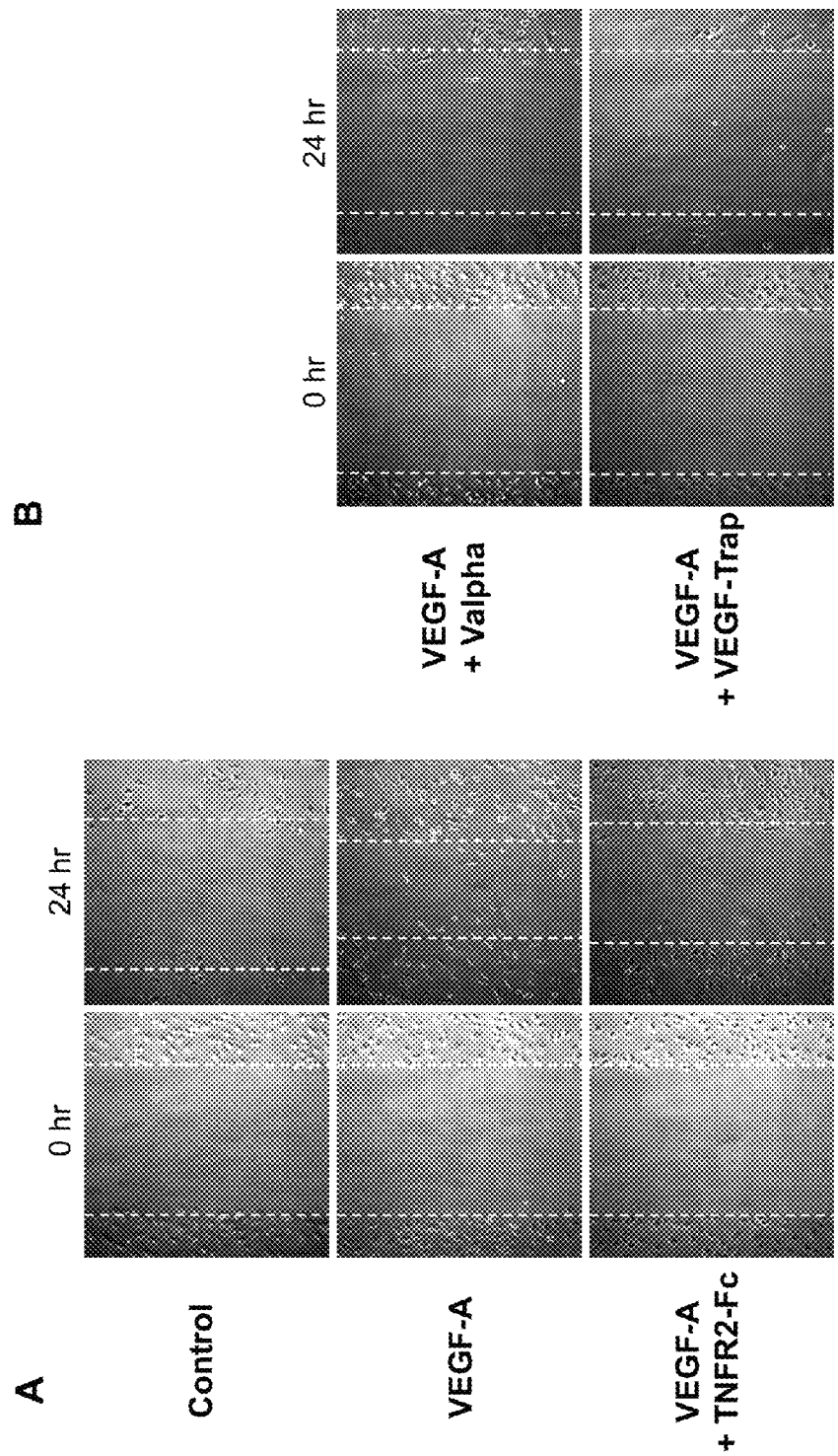
FIGS. 14A-14B show in vitro scratch assay for examination of Valpha in the VEGF-A-induced cell migration in the cultured HUVEC. Note that the cell migrating activity induced by the VEGF-A treatment was inhibited by Valpha or VEGF-Trap (B), but not by TNFR2-Fc protein (A).

Effect of Valpha on VEGF-Induced Endothelial Cell Migration Using In Vitro Scratch Assay To examine inhibitory activity of Valpha on VEGF, "in vitro scratch assay of human umbilical vein endothelial cells (HUVEC)" was tested (FIG. 14). HUVECs were cultured to confluence and a scratch was made using a sterile blue tip (1,000 µl). Detached cells were removed and dishes were treated with indicated proteins for 24 hr. The final concentration of VEGF-A was 50 ng/ml, whereas the final concentrations of TNFR2-Fc, Valpha, and VEGF-Trap were 2 µg/ml. Photograph images were taken at 0 hr and 24 hr after treatments of VEGF-A and each inhibitory protein (FIG. 14).

At 24 hr later, HUVEC treated PBS displayed no significant migration starting from the borderline, whereas HUVEC treated with VEGF (50 ng/ml) displayed significant cell migration (FIG. 14). The cell migrating activity induced by the VEGF-A treatment was inhibited by Valpha or VEGF-Trap, but not with TNFR2-Fc protein (FIG. 14), indicating that Valpha and VEGF-Trap has inhibitory effect in VEGF-induced cell migration.

Example 7

Effect of Valpha on TNF-α-Induced Cytotoxicity

Figure 15:
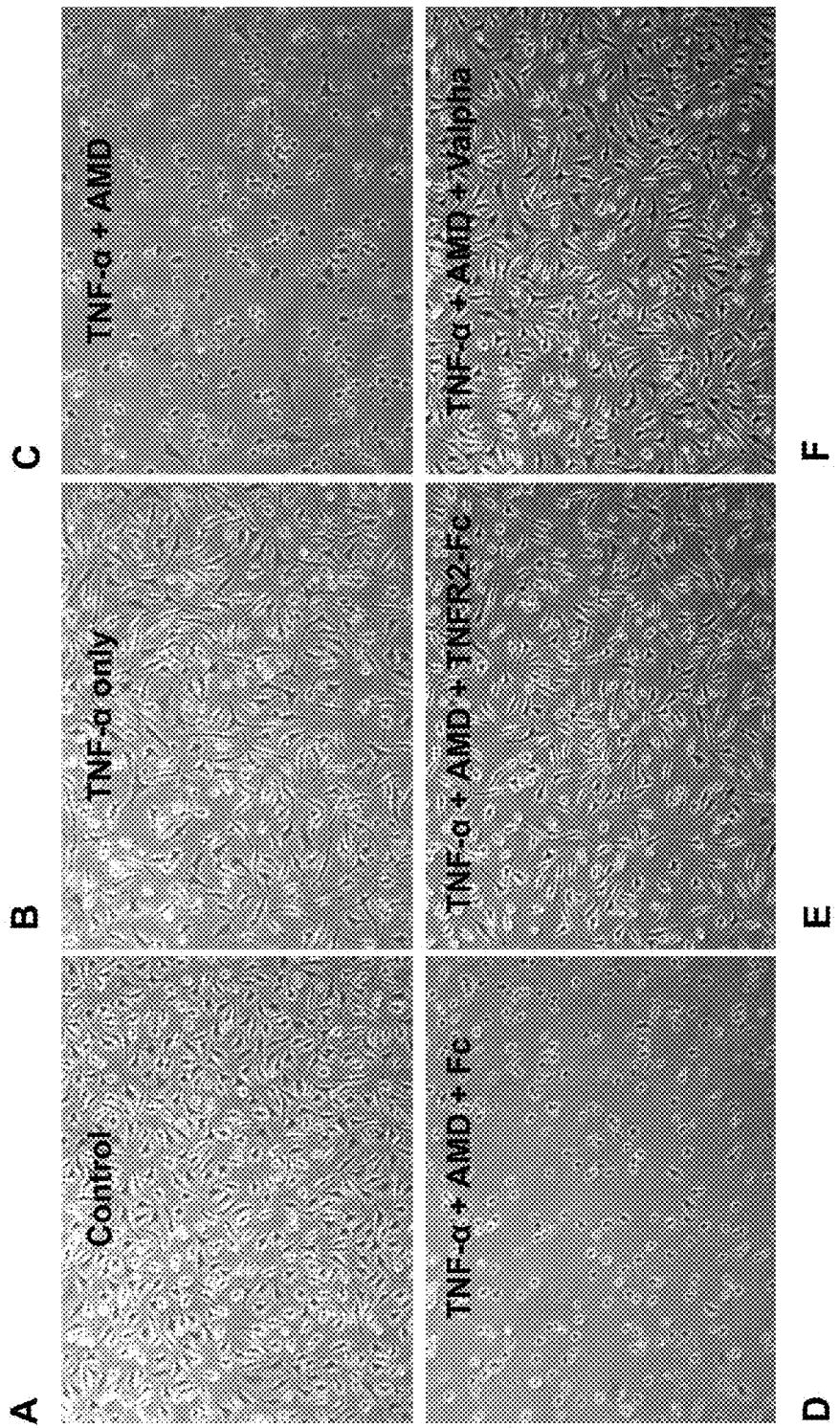
FIGS. 15A-15F show representative photographs of TNF-α-induced cytotoxicity on L929 murine fibrosarcoma. (A) is control, untreated cells. Dead floating cells were moderately observed in TNF-α treated sample of cells (B), whereas this TNF-α-induced cytotoxicity was enhanced in the presence of actinomycin-D (AMD) (C). Co-treatment of TNF-α and AMD with TNFR2-Fc (E) or Valpha attenuated TNF-α-induced cytotoxicity (F), whereas co-treatment with Fc protein (D) did not change the TNF-α-induced cytotoxicity.

To test the inhibitory effect of Valpha in TNF-α-induced biological action, TNF-α-induced cytotoxicity on L929 murine fibrosarcoma cells were tested (FIG. 15). L929 cells were cultured to confluence and treated with indicated protein for 24 hr. The final concentration of TNF-α was 1.0 ng/ml, whereas the final concentrations of TNFR2-Fc, Valpha, and VEGF-Trap were 1 µg/ml. The final concentration of actinomycin-D (AMD) was 2 µg/ml. Photographs using a phase-contrast microscope were taken at 24 hr after treatment with TNF-α and each inhibitory protein (FIG. 15).

At 24 hr later, the control L929 cells were healthy, whereas the TNF-α-treated cells were partially damaged and floated (FIG. 15). In comparison, the TNF-α-FAMD-treated cells and the TNF-α-FAMD+Fc-treated cells were almost completely damaged, whereas TNF-α-FAMD+TNFR2-Fc-treated cells and TNF-α-FAMD+Valpha-treated cells were not damaged at all (FIG. 15), indicating that Valpha has strong inhibitory effect on TNF-α-induced cytotoxicity on L929 murine fibrosarcoma cells.

For the quantitative analysis of inhibitory effect of Valpha on the TNF-α induced cytotoxicity L929 murine fibrosarcoma cells, MTT assay was performed (FIG. 16). L929 cells were seeded at 5×10⁵ cells/well in 96 well plate in DMEM containing 5% serum. One lane was left without the cells, and this lane was used as a control for the minimum absorbance. The plate was incubated overnight at 37° C. in humified incubator under 5% $CO_2$. Replacement of the medium with DMEM containing 2% serum and 2 μg/ml of actinomycin D for inhibition of extra cell growth. The plate was divided into two groups, one was TNF-α treated group, and the other was TNF-α (5 ng/ml)- and the indicated amounts of indicated recombinant protein-treated group. Serial diluted TNF-α (from 10 ng/ml to 0.0005 ng/ml) was incubated with the cells (FIG. 16A).

For MTT assay, the culture media were discarded and the plates were washed with PBS, followed by addition of 10 μl of MTT reagent into each well, and incubated at 37° C. for 4 hr. After washing, 70 μl of 0.2% HCl was added in isopropanol solution to dissolve formazan crystal. Reactive colors were analyzed at optical density 550 nm by ELISA reader (BioRad M680) and the viability percentage was calculated using "viability=(mean absorbance of sample)/(mean absorbance of control)×100" (FIG. 16).

The MTT assay revealed that the cells were damaged by TNF-α in a concentration dependent manner and the LD50 of TNF-α was ~0.01 ng/ml (FIG. 16A). Serial diluted (5-300 ng/ml) concentration of the recombinant proteins, Valpha, ENBREL®, REMICADE®, and VEGF-Trap differentially inhibited the TNF-α (5 ng/ml)-induced cells toxicities. The IC50 (mean±SE, n=4) of Valpha was 51±2.7, of ENBREL® was 35±2.3, of REMICADE® was 101±4.6, and of VEGF-Trap was out of range (FIG. 16B).

Example 8

Effect of Valpha on NF-κB Activity

TNF-α induces phosphorylation of p65, one subunit of NF-κB, and in turn this phosphorylated p65 is translocated from cytoplasm to nucleus in the TNF-α responsive cells. To examine inhibitory effect of Valpha on TNF-α-induced NF-κB activation in human lymphatic endothelial cells (hLECs), hLECs were seeded on gelatin coated sterilized glass coverslip in 24 well plate and cultured to confluence. Then, control, lipopolysaccharide (LPS, 500 ng/ml), TNF-α (1 ng/ml), or TNF-α (1 ng/ml)+Valpha (1 μg/ml) was treated to the cultured hLECs for 30 min, and nuclear translocalizations of NF-κB in the cells were examined by immunofluorescent staining (FIG. 17).

For the immunofluorescent staining of p65, the cells were fixed with 4% paraformaldehyde for 30 min at 4° C., and then the cells were washed with PBS and permeablized with PBS containing 0.05% of Triton X-100 (PBS-T) at 4° C. for 30 min and then washed with PBS. For blocking, 200 μl of 5% donkey serum was added to each well for 1 hr at room temperature. Then rabbit anti-human NF-κB p65 antibody (1:100 dilution; Santa Cruz, Cat# SC-109) was incubated with the cells for overnight at room temperature. After incubation of the primary antibody, the cells were washed with PBS and then incubated with donkey anti-rabbit FITC antibody (1:200 dilution; Jackson ImmunoResearch) for 2 hr at room temperature. For nuclear staining, the cells were incubated with DAPI (1:1000; Invitrogen) for 10 min at room temperature (FIG. 17).

Figure 17:
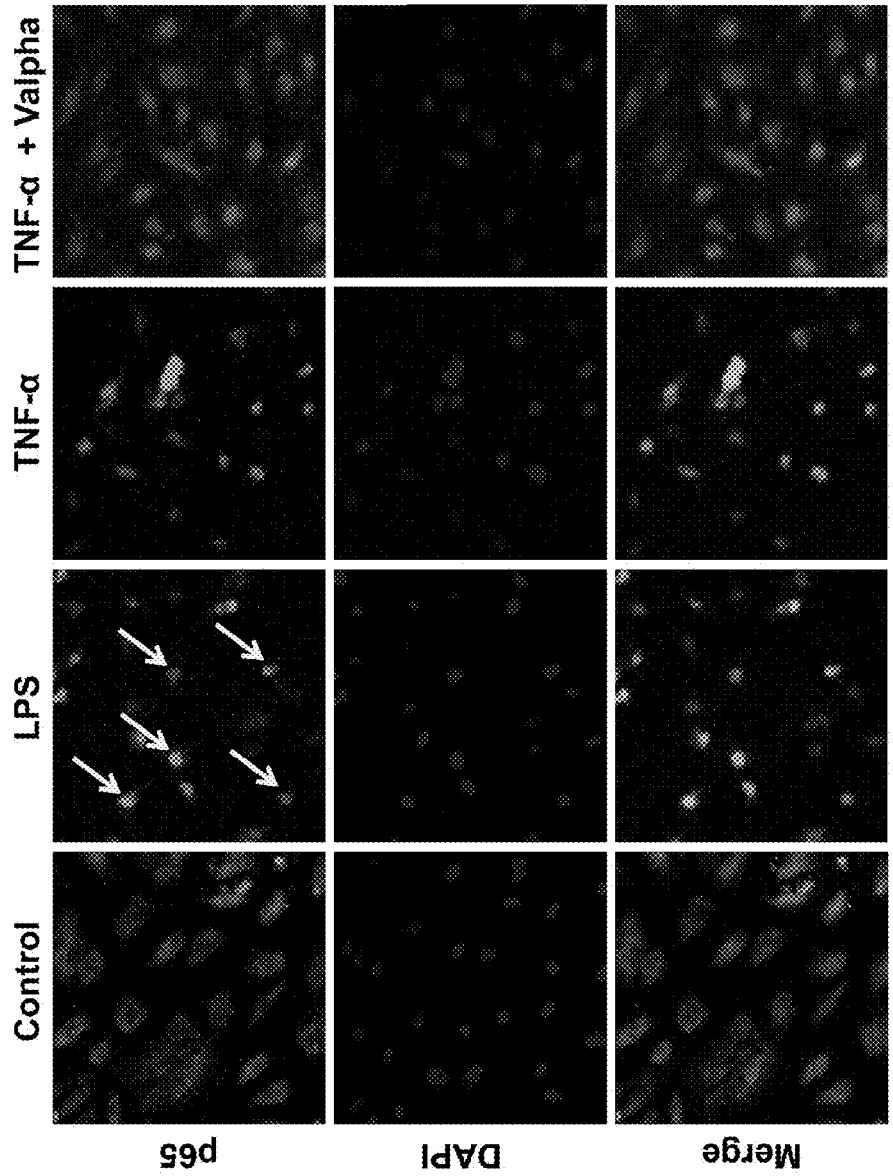
FIG. 17 depicts representative images for p65 of NF-κB translocalization in human lymphatic endothelial cells treated with Control (BSA), LPS, TNF-α, or TNF-α+Valpha. Note that LPS and TNF-α robustly induced nuclear translocalization of p65 (white arrow), whereas Valpha strongly inhibited the TNF-α-induced nuclear translocalization of p65 (TNF-α-induced NF-κB activation).

The immunofluorescent staining of p65 analysis revealed that Valpha strongly inhibited the TNF-α-induced NF-κB activation in hLECs (FIG. 17).

Example 9

Effect of Valpha on Retinopathy

Abnormal ocular angiogenesis accompanying vascular leakage and edema in retina is a main cause of diabetic retinopathy and age-related macular degeneration. Mouse model having abnormal ocular angiogenesis can be generated by exposure of neonatal mouse to hyperoxic atmosphere, that is "retinopathy of prematurity (ROP)" or "oxygen-induced retinopathy (OIR)" model (FIG. 18). ROP was introduced in C57/BL6 wild-type mice. Neonatal mice and their nursing mother were exposed to 75% oxygen (PRO-OX 110 chamber oxygen controller used) between postnatal day 7 (P7) and P12. This procedure produces vaso-obliteration and cessation of vascular development in the capillary beds of the central retina. Return of the animals to normoxia room air condition at P12 renders the ischemic and hypoxic central retina, and this procedure results in preretinal neovascularization. At P12, the mice received an intraocular injection of each protein (Control, VEGF-Trap, Valpha; 5 μg each) and sacrificed on P17.

Whole-mounts of retina and immunohistochemical staining for blood vessels were performed as follows. Eyeballs were enucleated from mice immediately and fixed in 1% paraformaldehyde (PFA) at 4° C. overnight. The retinas were isolated in PBS, blocked 1 hr at 25° C. with 0.3% Triton X-100 in TBS (TBS-T) containing 5% donkey serum (Jackson Immuno Research), and stained with biotin-conjugated isolectin B4 (Molecular Probes), rabbit anti-NG2 antibody (Millipore), rat anti-F4/80 antibody (eBioscience), and hamster anti-CD31 antibody (Millipore) overnight at 4° C. After washing six times in TBS-T, samples were incubated with Cy3-conjugated streptavidin (BD Pharmingen), FITC-conjugated anti-rabbit IgG antibody (Jackson Laboratory), Cy5-conjugated anti-rat IgG antibody (Jackson Laboratory), and Cy3-conjugated anti-hamster IgG antibody (Jackson Laboratory) for 4 hours at 25° C. Following another six times of washes in TBS-T, retinas were whole-mounted onto Superfrost/Plus microscope slides (12-550-15, Fisher) with the photoreceptor side down and embedded in VECTASHIELD (Vector) reagent.

Figure 19:
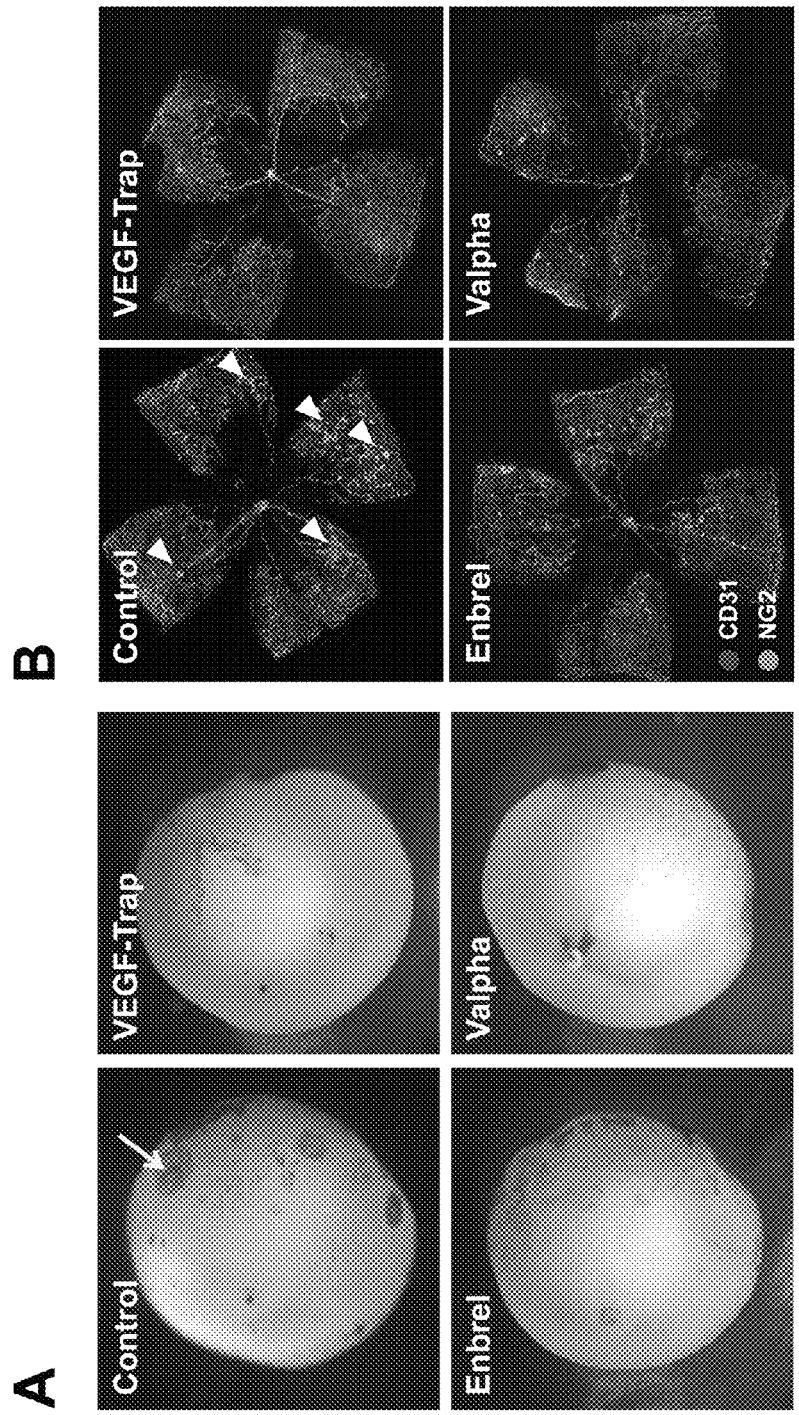
FIGS. 19A-19B show effects of Control, VEGF-Trap, ENBREL®, or Valpha on retinal vascular leakage (A) and vascular tufts formation in retina (B) in the mouse ROP model. Light microscopic analysis of hemorrhagic vascular leakage (white arrow) in the posterior surface of retina (FIG. 19A) and immunohistological analysis of preretinal vascular tufts formation (white arrow head) (FIG. 19B) are shown.
Figure 20:
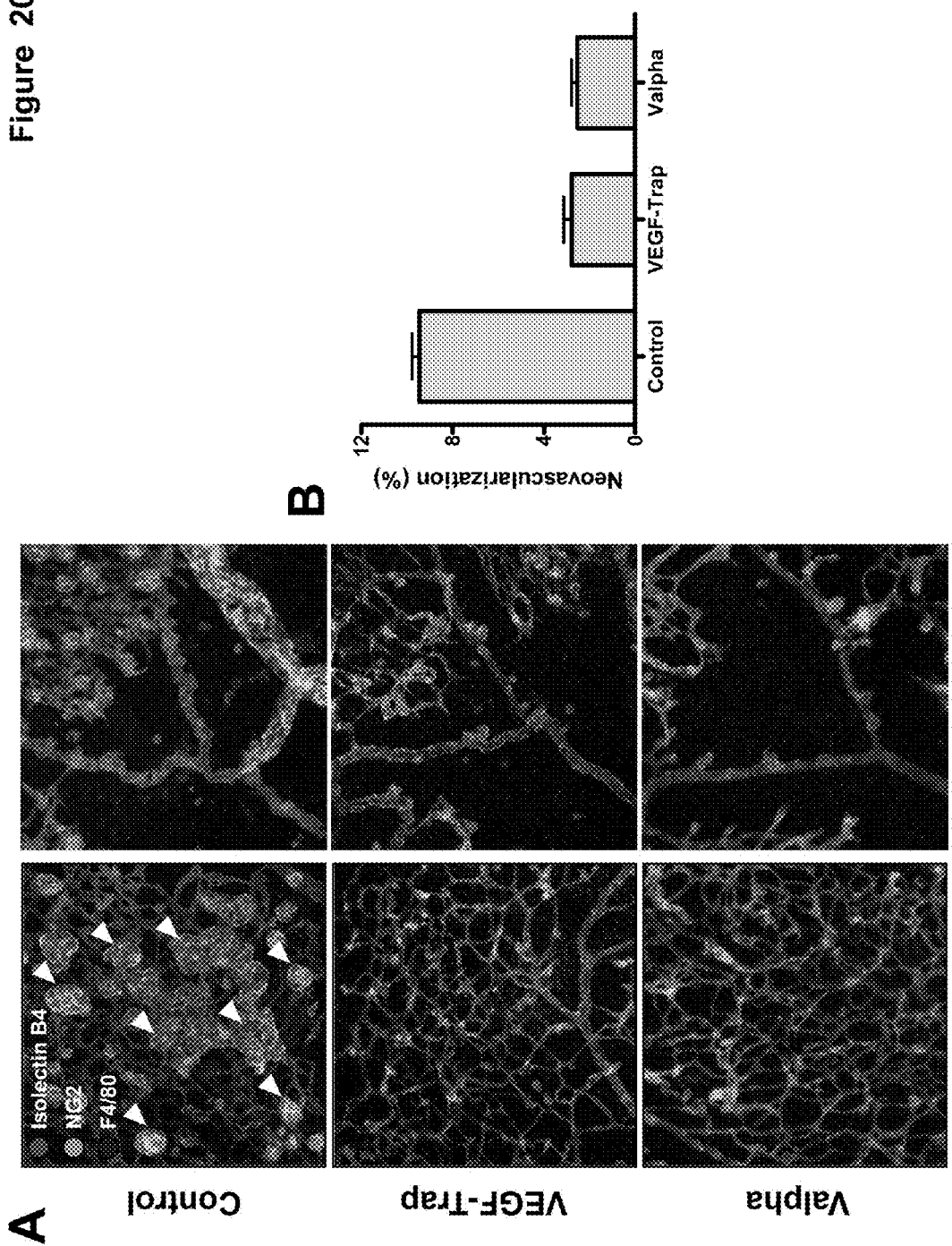
FIGS. 20A-20B show representative photographs of improving effects of Valpha on retinopathy model using mice (A), and bar graph showing neovascularization for Control, Valpha, and VEGF-Trap (B).

Number of preretinal vascular tufts in the retinal vessels, a typical feature of retinopathy, was highly increased in control group, whereas they were markedly reduced in VEGF-Trap- and Valpha-treated groups (FIG. 19). Blood vessel tortuosity was also highly increased in control group, whereas they were markedly reduced in VEGF-Trap- and Valpha-treated groups (FIG. 20). Quantification analysis revealed that ROP-induced formation of preretinal vascular tufts (white arrow head) caused by neovascularization in the retinal vessels were potently inhibited by treatment with VEGF-Trap or Valpha (FIG. 20B). However, number of F4/80+ macrophages was similar in VEGF-Trap-treated group compared to the control, whereas the number was markedly reduced in Valpha-treated group. The remaining macrophages in control and VEGF-Trap-treated groups may induce further pathological inflammatory process in the retina. Potency of Valpha was higher than VEGF-Trap in the reduction of ROP-induced F4/80+ macrophages infiltration to the retina with ROP. These data indicate that Valpha is more effective than VEGF-Trap for treating ROP in mouse. These data suggest that Valpha is an effective molecule for treating patients with AMD and diabetic-retinopathy.

Example 10

Effect of Valpha on Collagen-Induced Arthritis

Figure 21:
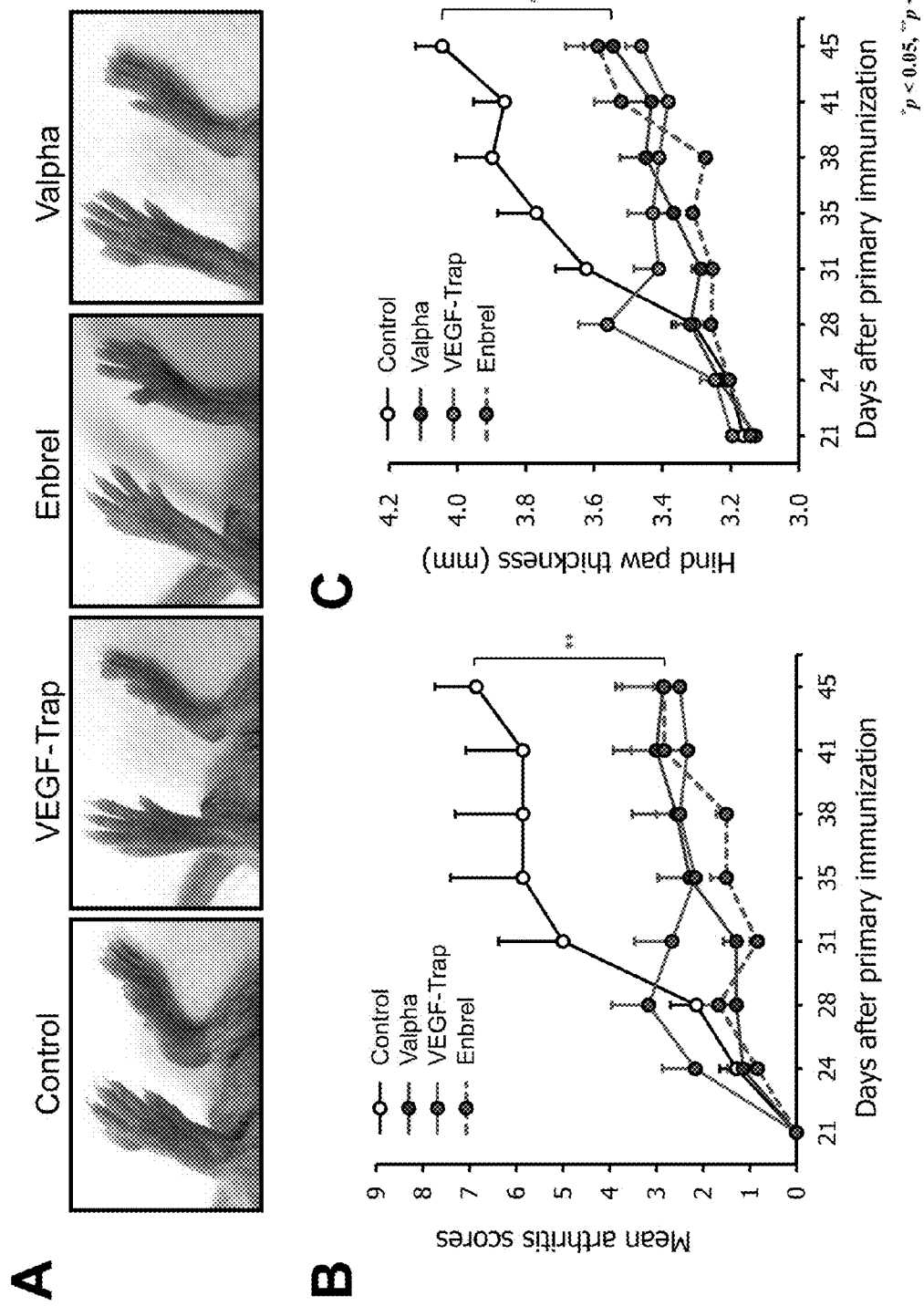
FIGS. 21A-21C show improving effects of Valpha on collagen-induced arthritis (CIA) model using mice. Photographs of Control, VEGF-Trap, ENBREL®, or Valpha administered mice is shown (A); Mean arthritis score graph is shown with respect to the administration of Control, VEGF-Trap, ENBREL®, or Valpha (B); and Hind paw thickness measurement graph is shown with respect to the administration of Control, VEGF-Trap, ENBREL®, or Valpha (C).
Figure 22:
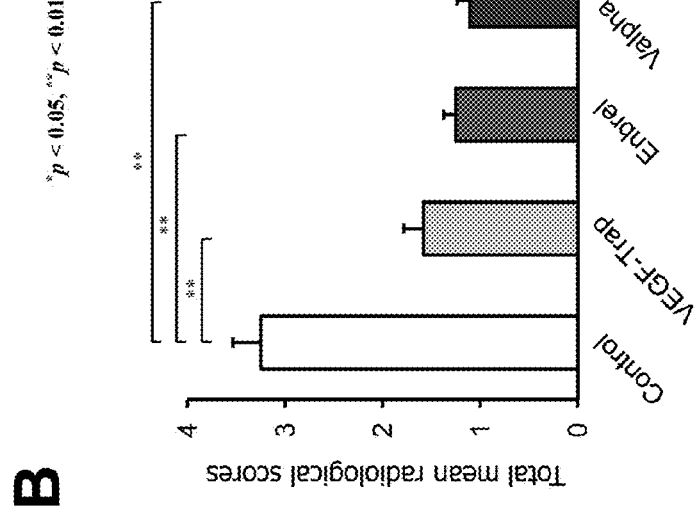
FIGS. 22A-22B show radiographic analysis regarding the effects of Control, VEGF-Trap, ENBREL®, or Valpha on collagen-induced arthritis (CIA) mouse model (A); and total mean radiological score is shown with respect to the administration of Control, VEGF-Trap, ENBREL®, or Valpha (B)

Inflammatory angiogenesis is a hallmark and a critical contributing factor in progression of rheumatoid arthritis (RA) (Lainer-Carr and Brahn, 2007, Nature Clinical Practice Rheumatology 3:434-442). Therefore, inhibition of inflammatory angiogenesis could be an effective method to reduce progression and joint destruction of RA. For induction of collagen-induced arthritis (CIA) to create an experimental mouse model of RA, male DBA/1J mice were immunized intradermally at the base of the tail with bovine type II collagen emulsified in an equal volume of complete Freund adjuvant. Three weeks later, the mice were immunologically boosted in the same manner. The mice with CIA were treated by subcutaneous injections of control, VEGF-Trap (25 mg/kg), ENBREL® (25 mg/kg), or Valpha (25 mg/kg) twice per week for 18 days from three weeks after the first immunization. Disease severity was clinically scored for each paw using following system: grade 0, no swelling; grade 1, slight swelling and erythema; grade 2, pronounced edema; grade 3, joint rigidity (FIG. 21). Radiographic analysis was performed using a modified radiographic imaging and the scores were determined in the knee, ankle, and tarsometatarsal joints (FIG. 22). VEGF-Trap, ENBREL®, and Valpha alleviated clinical scores and radiologic and histological abnormalities, whereas control buffer did not produce any ameliorative effects in the disease severity and joint destruction of CIA. Thus, Valpha is potential therapeutic agent to treat the patients with RA.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

TABLE 1

Valpha FV#1

```
              10             20             30             40             50             60
               *              *              *              *              *              *
ATG GCG CCC GTC GCC GTC TGG GCC GCG CTG GCC GTC GGA CTG GAG CTC TGG GCT GCG GCG
TAC CGC GGG CAG CGG CAG ACC CGG CGC GAC CGG CAG CCT GAC CTC GAG ACC CGA CGC CGC
Met Ala Pro Val Ala Val Trp Ala Ala Leu Ala Val Gly Leu Glu Leu Trp Ala Ala Ala
1               5             hTNFR2 SIGNAL SEQUENCE        15                          20

70             80             90            100            110            120
               *              *              *              *              *              *
CAC GCC TTG CCC GCC CAG GTG GCA TTT ACA CCC TAC GCC CCG GAG CCC GGG AGC ACA TGC
GTG CGG AAC GGG CGG GTC CAC CGT AAA TGT GGG ATG CGG GGC CTC GGG CCC TCG TGT ACG
His Ala Leu Pro Ala Gln Val Ala Phe Thr Pro Tyr Ala Pro Glu Pro Gly Ser Thr Cys
21_22 23        25            TNFR-Cys DOMAIN 1     35                              40

130            140            150            160            170            180
               *              *              *              *              *              *
CGG CTA AGA GAA TAC TAT GAC CAG ACA GCT CAG ATG TGC TGC AGC AAA TGC TCG CCG GGC
GCC GAT TCT CTT ATG ATA CTG GTC TGT CGA GTC TAC ACG ACG TCG TTT ACG AGC GGC CCG
Arg Leu Arg Glu Tyr Tyr Asp Gln Thr Ala Gln Met Cys Cys Ser Lys Cys Ser Pro Gly
41                45            TNFR-Cys DOMAIN 1     55                            60

190            200            210            220            230            240
               *              *              *              *              *              *
CAA CAT GCA AAA GTC TTC TGT ACC AAG ACC TCG GAC ACC GTG TGT GAC TCC TGT GAG GAC
GTT GTA CGT TTT CAG AAG ACA TGG TTC TGG AGC CTG TGG CAC ACA CTG AGG ACA CTC CTG
Gln His Ala Lys Val Phe Cys Thr Lys Thr Ser Asp Thr Val Cys Asp Ser Cys Glu Asp
61                65            TNFR-Cys DOMAIN 1     75_76  77                     80

250            260            270            280            290            300
               *              *              *              *              *              *
AGC ACA TAC ACC CAG CTC TGG AAC TGG GTT CCC GAG TGC TTG AGC TGT GGC TCC CGC TGT
TCG TGT ATG TGG GTC GAG ACC TTG ACC CAA GGG CTC ACG AAC TCG ACA CCG AGG GCG ACA
Ser Thr Tyr Thr Gln Leu Trp Asn Trp Val Pro Glu Cys Leu Ser Cys Gly Ser Arg Cys
81                85            TNFR-Cys DOMAIN 2     95                            100

310            320            330            340            350            360
               *              *              *              *              *              *
AGC TCT GAC CAG GTG GAA ACT CAA GCC TGC ACT CGG GAA CAG AAC CGC ATC TGC ACC TGC
TCG AGA CTG GTC CAC CTT TGA GTT CGG ACG TGA GCC CTT GTC TTG GCG TAG ACG TGG ACG
Ser Ser Asp Gln Val Glu Thr Gln Ala Cys Thr Arg Glu Gln Asn Arg Ile Cys Thr Cys
101               105           TNFR-Cys DOMAIN 2     115           118 119_120

370            380            390            400            410            420
               *              *              *              *              *              *
AGG CCC GGC TGG TAC TGC GCG CTG AGC AAG CAG GAG GGG TGC CGG CTG TGC GCG CCG CTG
TCC GGG CCG ACC ATG ACG CGC GAC TCG TTC GTC CTC CCC ACG GCC GAC ACG CGC GGC GAC
Arg Pro Gly Trp Tyr Cys Ala Leu Ser Lys Gln Glu Gly Cys Arg Leu Cys Ala Pro Leu
121 122           125           TNFR-Cys DOMAIN 3     135                           140
```

TABLE 1-continued

Valpha FV#1

```
        430         440         450         460         470         480
         ★           ★           ★           ★           ★           ★
CGC AAG TGC CGC CCG GGC TTC GGC GTG GCC AGA CCA GGA ACT GAA ACA TCA GAC GTG GTG
GCG TTC ACG GCG GGC CCG AAG CCG CAC CGG TCT GGT CCT TGA CTT TGT AGT CTG CAC CAC
Arg Lys Cys Arg Pro Gly Phe Gly Val Ala Arg Pro Gly Thr Glu Thr Ser Asp Val Val
141_____145_____TNFR-Cys DOMAIN 3_____155_____160

490         500         510         520         530         540
         ★           ★           ★           ★           ★           ★
TGC AAG CCC TGT GCC CCG GGG ACG TTC TCC AAC ACG ACT TCA TCC ACG GAT ATT TGC AGG
ACG TTC GGG ACA CGG GGC CCC TGC AAG AGG TTG TGC TGA AGT AGG TGC CTA TAA ACG TCC
Cys Lys Pro Cys Ala Pro Gly Thr Phe Ser Asn Thr Thr Ser Ser Thr Asp Ile Cys Arg
161_162 163_____165_____TNFR-Cys DOMAIN 4_____175_____180

550         560         570         580         590         600
         ★           ★           ★           ★           ★           ★
CCC CAC CAG ATC TGT AAC GTG GTG GCC ATC CCT GGG AAT GCA AGC ATG GAT GCA GTC TGC
GGG GTG GTC TAG ACA TTG CAC CAC CGG TAG GGA CCC TTA CGT TCG TAC CTA CGT CAG ACG
Pro His Gln Ile Cys Asn Val Val Ala Ile Pro Gly Asn Ala Ser Met Asp Ala Val Cys
181_____185_____TNFR-Cys DOMAIN 4_____195_____200

610         620         630         640         650         660
         ★           ★           ★           ★           ★           ★
ACG TCC ACG TCC CCC ACC CGG AGT ATG GCC CCA GGG GCA GTA CAC TTA CCC CAG CCA GTG
TGC AGG TGC AGG GGG TGG GCC TCA TAC CGG GGT CCC CGT CAT GTG AAT GGG GTC GGT CAC
Thr Ser Thr Ser Pro Thr Arg Ser Met Ala Pro Gly Ala Val His Leu Pro Gln Pro Val
201 202_____205_____hTNFR2 LINKER_____215_____220

670         680         690         700         710         720
         ★           ★           ★           ★           ★           ★
TCC ACA CGA TCC CAA CAC ACG CAG CCA ACT CCA GAA CCC AGC ACT GCT CCA AGC ACC TCC
AGG TGT GCT AGG GTT GTG TGC GTC GGT TGA GGT CTT GGG TCG TGA CGA GGT TCG TGG AGG
Ser Thr Arg Ser Gln His Thr Gln Pro Thr Pro Glu Pro Ser Thr Ala Pro Ser Thr Ser
221_____225_____hTNFR2 LINKER_____235_____240

730         740         750         760         770         780
         ★           ★           ★           ★           ★           ★
TTC CTG CTC CCA ATG GGC CCC AGC CCC CCA GCT GAA GGG AGC ACT GGC GAC GGT AGA CCT
AAG GAC GAG GGT TAC CCG GGG TCG GGG GGT CGA CTT CCC TCG TGA CCG CTG CCA TCT GGA
Phe Leu Leu Pro Met Gly Pro Ser Pro Pro Ala Glu Gly Ser Thr Gly Asp Gly Arg Pro
241_____245_____hTNFR2 LINKER_____255_____257 258_____260

790         800         810         820         830         840
         ★           ★           ★           ★           ★           ★
TTC GTA GAG ATG TAC AGT GAA ATC CCC GAA ATT ATA CAC ATG ACT GAA GGA AGG GAG CTC
AAG CAT CTC TAC ATG TCA CTT TAG GGG CTT TAA TAT GTG TAC TGA CTT CCT TCC CTC GAG
Phe Val Glu Met Tyr Ser Glu Ile Pro Glu Ile Ile His Met Thr Glu Gly Arg Glu Leu
261_____265_____hVEGFR1 IG DOMAIN 2_____275_____280

850         860         870         880         890         900
         ★           ★           ★           ★           ★           ★
GTC ATT CCC TGC CGG GTT ACG TCA CCT AAC ATC ACT GTT ACT TTA AAA AAG TTT CCA CTT
CAG TAA GGG ACG GCC CAA TGC AGT GGA TTG TAG TGA CAA TGA AAT TTT TTC AAA GGT GAA
Val Ile Pro Cys Arg Val Thr Ser Pro Asn Ile Thr Val Thr Leu Lys Lys Phe Pro Leu
281_____285_____hVEGFR1 IG DOMAIN 2_____295_____300

910         920         930         940         950         960
         ★           ★           ★           ★           ★           ★
GAC ACT TTG ATC CCT GAT GGA AAA CGC ATA ATC TGG GAC AGT AGA AAG GGC TTC ATC ATA
CTG TGA AAC TAG GGA CTA CCT TTT GCG TAT TAG ACC CTG TCA TCT TTC CCG AAG TAG TAT
Asp Thr Leu Ile Pro Asp Gly Lys Arg Ile Ile Trp Asp Ser Arg Lys Gly Phe Ile Ile
301_____305_____hVEGFR1 IG DOMAIN 2_____315_____320

970         980         990        1000        1010        1020
         ★           ★           ★           ★           ★           ★
TCA AAT GCA ACG TAC AAA GAA ATA GGG CTT CTG ACC TGT GAA GCA ACA GTC AAT GGG CAT
AGT TTA CGT TGC ATG TTT CTT TAT CCC GAA GAC TGG ACA CTT CGT TGT CAG TTA CCC GTA
Ser Asn Ala Thr Tyr Lys Glu Ile Gly Leu Leu Thr Cys Glu Ala Thr Val Asn Gly His
321_____325_____hVEGFR1 IG DOMAIN 2_____335_____340

1030        1040        1050        1060        1070        1080
         ★           ★           ★           ★           ★           ★
TTG TAT AAG ACA AAC TAT CTC ACA CAT CGA CAA CTC GAG GAC AAA ACT CAC ACA TGC CCA
AAC ATA TTC TGT TTG ATA GAG TGT GTA GCT GTT GAG CTC CTG TTT TGA GTG TGT ACG GGT
Leu Tyr Lys Thr Asn Tyr Leu Thr His Arg Gln Leu Glu Asp Lys Thr His Thr Cys Pro
341_____hVEGFR1 IG DOMAIN 2_____350_351 352_____hFC DOMAIN_____360
```

TABLE 1-continued

Valpha FV#1

```
           1090            1100            1110            1120            1130            1140
            *               *               *               *               *               *
CCG TGC CCA GCA CCT GAA CTC CTG GGG GGA CCG TCA GTC TTC CTC TTC CCC CCA AAA CCC
GGC ACG GGT CGT GGA CTT GAG GAC CCC CCT GGC AGT CAG AAG GAG AAG GGG GGT TTT GGG
Pro Cys Pro Ala Pro Glu Leu Leu Gly Gly Pro Ser Val Phe Leu Phe Pro Pro Lys Pro
361_____365_____hFC DOMAIN_____375_____380

1150            1160            1170            1180            1190            1200
            *               *               *               *               *               *
AAG GAC ACC CTC ATG ATC TCC CGG ACC CCT GAG GTC ACA TGC GTG GTG GTG GAC GTG AGC
TTC CTG TGG GAG TAC TAG AGG GCC TGG GGA CTC CAG TGT ACG CAC CAC CAC CTG CAC TCG
Lys Asp Thr Leu Met Ile Ser Arg Thr Pro Glu Val Thr Cys Val Val Val Asp Val Ser
381_____385_____hFC DOMAIN_____395_____400

1210            1220            1230            1240            1250            1260
            *               *               *               *               *               *
CAC GAA GAC CCT GAG GTC AAG TTC AAC TGG TAC GTG GAC GGC GTG GAG GTG CAT AAT GCC
GTG CTT CTG GGA CTC CAG TTC AAG TTG ACC ATG CAC CTG CCG CAC CTC CAC GTA TTA CGG
His Glu Asp Pro Glu Val Lys Phe Asn Trp Tyr Val Asp Gly Val Glu Val His Asn Ala
401_____405_____hFC DOMAIN_____415_____420

1270            1280            1290            1300            1310            1320
            *               *               *               *               *               *
AAG ACA AAG CCG CGG GAG GAG CAG TAC AAC AGC ACG TAC CGT GTG GTC AGC GTC CTC ACC
TTC TGT TTC GGC GCC CTC CTC GTC ATG TTG TCG TGC ATG GCA CAC CAG TCG CAG GAG TGG
Lys Thr Lys Pro Arg Glu Glu Gln Tyr Asn Ser Thr Tyr Arg Val Val Ser Val Leu Thr
421_____425_____hFC DOMAIN_____435_____440

1330            1340            1350            1360            1370            1380
            *               *               *               *               *               *
GTC CTG CAC CAG GAC TGG CTG AAT GGC AAG GAG TAC AAG TGC AAG GTC TCC AAC AAA GCC
CAG GAC GTG GTC CTG ACC GAC TTA CCG TTC CTC ATG TTC ACG TTC CAG AGG TTG TTT CGG
Val Leu His Gln Asp Trp Leu Asn Gly Lys Glu Tyr Lys Cys Lys Val Ser Asn Lys Ala
441_____445_____hFC DOMAIN_____455_____460

1390            1400            1410            1420            1430            1440
            *               *               *               *               *               *
CTC CCA GCC CCC ATC GAG AAA ACC ATC TCC AAA GCC AAA GGG CAG CCC CGA GAA CCA CAG
GAG GGT CGG GGG TAG CTC TTT TGG TAG AGG TTT CGG TTT CCC GTC GGG GCT CTT GGT GTC
Leu Pro Ala Pro Ile Glu Lys Thr Ile Ser Lys Ala Lys Gly Gln Pro Arg Glu Pro Gln
461_____465_____hFC DOMAIN_____475_____480

1450            1460            1470            1480            1490            1500
            *               *               *               *               *               *
GTG TAC ACC CTG CCC CCA TCC CGG GAG GAG ATG ACC AAG AAC CAG CTG AGC CTG ACC TGC
CAC ATG TGG GAC GGG GGT AGG GCC CTC CTC TAC TGG TTC TTG GTC GAC TCG GAC TGG ACG
Val Tyr Thr Leu Pro Pro Ser Arg Glu Glu Met Thr Lys Asn Gln Val Ser Leu Thr Cys
481_____485_____hFC DOMAIN_____495_____500

1510            1520            1530            1540            1550            1560
            *               *               *               *               *               *
CTG GTC AAA GGC TTC TAT CCC AGC GAC ATC GCC GTG GAG TGG GAG AGC AAT GGG CAG CCG
GAC CAG TTT CCG AAG ATA GGG TCG CTG TAG CGG CAC CTC ACC CTC TCG TTA CCC GTC GGC
Leu Val Lys Gly Phe Tyr Pro Ser Asp Ile Ala Val Glu Trp Glu Ser Asn Gly Gln Pro
501_____505_____hFC DOMAIN_____515_____520

1570            1580            1590            1600            1610            1620
            *               *               *               *               *               *
GAG AAC AAC TAC AAG ACC ACG CCT CCC GTG CTG GAC TCC GAC GGC TCC TTC TTC CTC TAC
CTC TTG TTG ATG TTC TGG TGC GGA GGG CAC GAC CTG AGG CTG CCG AGG AAG AAG GAG ATG
Glu Asn Asn Tyr Lys Thr Thr Pro Pro Val Leu Asp Ser Asp Gly Ser Phe Phe Leu Tyr
521_____525_____hFC DOMAIN_____535_____540

1630            1640            1650            1660            1670            1680
            *               *               *               *               *               *
AGC AAG CTC ACC GTG GAC AAG AGC AGG TGG CAG CAG GGG AAC GTC TTC TCA TGC TCC GTG
TCG TTC GAG TGG CAC CTG TTC TCG TCC ACC GTC GTC CCC TTG CAG AAG AGT ACG AGG CAC
Ser Lys Leu Thr Val Asp Lys Ser Arg Trp Gln Gln Gly Asn Val Phe Ser Cys Ser Val
541_____545_____hFC DOMAIN_____555_____560

1690            1700            1710            1720            1730            1740
            *               *               *               *               *               *
ATG CAT GAG GCT CTG CAC AAC CAC TAC ACG CAG AAG AGC CTC TCC CTG TCT CCG GGT AAA
TAC GTA CTC CGA GAC GTG TTG GTG ATG TGC GTC TTC TCG GAG AGG GAC AGA GGC CCA TTT
Met His Glu Ala Leu His Asn His Tyr Thr Gln Lys Ser Leu Ser Leu Ser Pro Gly Lys
561_____565_____hFC DOMAIN_____575_____580
```

TABLE 1-continued

Valpha FV#1

```
1743
 ★
TGA (SEQ ID NO: 1)
ACT
*** (SEQ ID NO: 2)
581
```

TABLE 2

Valpha VF#1

```
         10            20            30            40            50            60
          ★             ★             ★             ★             ★             ★
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAG GAA GAG
Met Val Ser Tyr Trp Asp Thr Gly Val Leu Leu Cys Ala Leu Leu Ser Cys Leu Leu Leu
1_____5_____hVEGFR1 SIGNAL SEQUENCE10_____15_____20

70            80            90           100           110           120
          ★             ★             ★             ★             ★             ★
ACA GGA TCT AGT TCA GGT GGT AGA CCT TTC GTA GAG ATG TAC AGT GAA ATC CCC GAA ATT
TGT CCT AGA TCA AGT CCA CCA TCT GGA AAG CAT CTC TAC ATG TCA CTT TAG GGG CTT TAA
Thr Gly Ser Ser Ser Gly Gly Arg Pro Phe Val Glu Met Tyr Ser Glu Ile Pro Glu Ile
21_____25__26  27_____hVEGFR1 IG DOMAIN 2_____40

130           140           150           160           170           180
          ★             ★             ★             ★             ★             ★
ATA CAC ATG ACT GAA GGA AGG GAG CTC GTC ATT CCC TGC CGG GTT ACG TCA CCT AAC ATC
TAT GTG TAC TGA CTT CCT TCC CTC GAG CAG TAa GGG ACG GCC CAA TGC AGT GGA TTG TAG
Ile His Met Thr Glu Gly Arg Glu Leu Val Ile Pro Cys Arg Val Thr Ser Pro Asn Ile
41_____45_____hVEGFR1 IG DOMAIN 2_____55_____60

190           200           210           220           230           240
          ★             ★             ★             ★             ★             ★
ACT GTT ACT TTA AAA AAG TTT CCA CTT GAC ACT TTG ATC CCT GAT GGA AAA CGC ATA ATC
TGA CAA TGA AAT TTT TTC AAA GGT GAA CTG TGA AAC TAG GGA CTA CCT TTT GCG TAT TAG
Thr Val Thr Leu Lys Lys Phe Pro Leu Asp Thr Leu Ile Pro Asp Gly Lys Arg Ile Ile
61_____65_____hVEGFR1 IG DOMAIN 2_____75_____80

250           260           270           280           290           300
          ★             ★             ★             ★             ★             ★
TGG GAC AGT AGA AAG GGC TTC ATC ATA TCA AAT GCA ACG TAC AAA GAA ATA GGG CTT CTG
ACC CTG TCA TCT TTC CCG AAG TAG TAT AGT TTA CGT TGC ATG TTT CTT TAT CCC GAA GAC
Trp Asp Ser Arg Lys Gly Phe Ile Ile Ser Asn Ala Thr Tyr Lys Glu Ile Gly Leu Leu
81_____85_____hVEGFR1 IG DOMAIN 2_____95_____100

310           320           330           340           350           360
          ★             ★             ★             ★             ★             ★
ACC TGT GAA GCA ACA GTC AAT GGG CAT TTG TAT AAG ACA AAC TAT CTC ACA CAT CGA CAA
TGG ACA CTT CGT TGT CAG TTA CCC GTA AAC ATA TTC TGT TTG ATA GAG TGT GTA GCT GTT
Thr Cys Glu Ala Thr Val Asn Gly His Leu Tyr Lys Thr Asn Tyr Leu Thr His Arg Gln
101_____105_____hVEGFR1 IG DOMAIN 2_____115_____120

370           380           390           400           410           420
          ★             ★             ★             ★             ★             ★
TTG CCC GCC CAG GTG GCA TTT ACA CCC TAC GCC CCG GAG CCC GGG AGC ACA TGC CGG CTC
AAC GGG CGG GTC CAC CGT AAA TGT GGG ATG CGG GGC CTC GGG CCC TCG TGT ACG GCC GAG
Leu Pro Ala Gln Val Ala Phe Thr Pro Tyr Ala Pro Glu Pro Gly Ser Thr Cys Arg Leu
121_____125_____TNFR-CYS DOMAIN 1_____135_____140

430           440           450           460           470           480
          ★             ★             ★             ★             ★             ★
AGA GAA TAC TAT GAC CAG ACA GCT CAG ATG TGC TGC AGC AAA TGC TCG CCG GGC CAA CAT
TCT CTT ATG ATA CTG GTC TGT CGA GTC TAC ACG ACG TCG TTT ACG AGC GGC CCG GTT GTA
Arg Glu Tyr Tyr Asp Gln Thr Ala Gln Met Cys Cys Ser Lys Cys Ser Pro Gly Gln His
141_____145_____TNFR-CYS DOMAIN 1_____155_____160

490           500           510           520           530           540
          ★             ★             ★             ★             ★             ★
GCA AAA GTC TTC TGT ACC AAG ACC TCG GAC ACC GTG TGT GAC TCC TGT GAG GAC AGC ACA
CGT TTT CAG AAG ACA TGG TTC TGG AGC CTG TGG CAC ACA CTG AGG ACA CTC CTG TCG TGT
Ala Lys Val Phe Cys Thr Lys Thr Ser Asp Thr Val Cys Asp Ser Cys Glu Asp Ser Thr
161_____165_____TNFR-CYS DOMAIN 1___174 175_____180
```

TABLE 2-continued

Valpha VF#1

```
            550           560           570           580           590           600
             *             *             *             *             *             *
TAC ACC CAG CTC TGG AAC TGG GTT CCC GAG TGC TTG AGC TGT GGC TCC CGC TGT AGC TCT
ATG TGG GTC GAG ACC TTG ACC CAA GGG CTC ACG AAC TCG ACA CCG AGG GCG ACA TCG AGA
Tyr Thr Gln Leu Trp Asn Trp Val Pro Glu Cys Leu Ser Cys Gly Ser Arg Cys Ser Ser
181_____185_____TNFR-CYS DOMAIN 2_____195_____200

610           620           630           640           650           660
             *             *             *             *             *             *
GAC CAG GTG GAA ACT CAA GCC TGC ACT CGG GAA CAG AAC CGC ATC TGC ACC TGC AGG CCC
CTG GTC CAC CTT TGA GTT CGG ACG TGA GCC CTT GTC TTG GCG TAG ACG TGG ACG TCC GGG
Asp Gln Val Glu Thr Gln Ala Cys Thr Arg Glu Gln Asn Arg Ile Cys Thr Cys Arg Pro
201_____205_____TNFR-Cys DOMAIN 2_____215_____219 220

670           680           690           700           710           720
             *             *             *             *             *             *
GGC TGG TAC TGC GCG CTG AGC AAG CAG GAG GGG TGC CGG CTG TGC GCG CCG CTG CGC AAG
CCG ACC ATG ACG CGC GAC TCG TTC GTC CTC CCC ACG GCC GAC ACG CGC GGC GAC GCG TTC
Gly Trp Tyr Cys Ala Leu Ser Lys Gln Glu Gly Cys Arg Leu Cys Ala Pro Leu Arg Lys
221_____225_____TNFR-Cys DOMAIN 3_____235_____240

730           740           750           760           770           780
             *             *             *             *             *             *
TGC CGC CCG GGC TTC GGC GTG GCC AGA CCA GGA ACT GAA ACA TCA GAC GTG GTG TGC AAG
ACG GCG GGC CCG AAG CCG CAC CGG TCT GGT CCT TGA CTT TGT AGT CTG CAC CAC ACG TTC
Cys Arg Pro Gly Phe Gly Val Ala Arg Pro Gly Thr Glu Thr Ser Asp Val Val Cys Lys
241_____245_____TNFR-Cys DOMAIN 3_____255_____260

790           800           810           820           830           840
             *             *             *             *             *             *
CCC TGT GCC CCG GGG ACG TTC TCC AAC ACG ACT TCA TCC ACG GAT ATT TGC AGG CCC CAC
GGG ACA CGG GGC CCC TGC AAG AGG TTG TGC TGA AGT AGG TGC CTA TAA ACG TCC GGG GTG
Pro Cys Ala Pro Gly Thr Phe Ser Asn Thr Thr Ser Ser Thr Asp Ile Cys Arg Pro His
261_____265_____TNFR-Cys DOMAIN 4_____275_____280

850           860           870           880           890           900
             *             *             *             *             *             *
CAG ATC TGT AAC GTG GTG GCC ATC CCT GGG AAT GCA AGC ATG GAT GCA GTC TGC ACG TCC
GTC TAG ACA TTG CAC CAC CGG TAG GGA CCC TTA CGT TCG TAC CTA CGT CAG ACG TGC AGG
Gln Ile Cys Asn Val Val Ala Ile Pro Gly Asn Ala Ser Met Asp Ala Val Cys Thr Ser
281_____285_____TNFR-Cys DOMAIN 4_____295_____299 300

910           920           930           940           950           960
             *             *             *             *             *             *
ACG TCC CCC ACC CGG AGT ATG GCC CCA GGG GCA GTA CAC TTA CCC CAG CCA GTG TCC ACA
TGC AGG GGG TGG GCC TCA TAC CGG GGT CCC CGT CAT GTG AAT GGG GTC GGT CAC AGG TGT
Thr Ser Pro Thr Arg Ser Met Ala Pro Gly Ala Val His Leu Pro Gln Pro Val Ser Thr
301_____305_____hTNFR2 LINKER_____315_____320

970           980           990          1000          1010          1020
             *             *             *             *             *             *
CGA TCC CAA CAC ACG CAG CCA ACT CCA GAA CCC AGC ACT GCT CCA AGC ACC TCC TTC CTG
GCT AGG GTT GTG TGC GTC GGT TGA GGT CTT GGG TCG TGA CGA GGT TCG TGG AGG AAG GAC
Arg Ser Gln His Thr Gln Pro Thr Pro Glu Pro Ser Thr Ala Pro Ser Thr Ser Phe Leu
321_____325_____hTNFR2 LINKER_____335_____340

1030          1040          1050          1060          1070          1080
             *             *             *             *             *             *
CTC CCA ATG GGC CCC AGC CCC CCA GCT GAA GGG AGC ACT GGC GAC CTC GAG GAC AAA ACT
GAG GGT TAC CCG GGG TCG GGG GGT CGA CTT CCC TCG TGA CCG CTG GAG CTC CTG TTT TGA
Leu Pro Met Gly Pro Ser Pro Pro Ala Glu Gly Ser Thr Gly Asp Leu Glu Asp Lys Thr
341_____345_____hTNFR2 LINKER_____355 356_hFC DOMAIN___360

1090          1100          1110          1120          1130          1140
             *             *             *             *             *             *
CAC ACA TGC CCA CCG TGC CCA GCA CCT GAA CTC CTG GGG GGA CCG TCA GTC TTC CTC TTC
GTG TGT ACG GGT GGC ACG GGT CGT GGA CTT GAG GAC CCC CCT GGC AGT CAG AAG GAG AAG
His Thr Cys Pro Pro Cys Pro Ala Pro Glu Leu Leu Gly Gly Pro Ser Val Phe Leu Phe
361_____365_____hFC DOMAIN_____375_____380

1150          1160          1170          1180          1190          1200
             *             *             *             *             *             *
CCC CCA AAA CCC AAG GAC ACC CTC ATG ATC TCC CGG ACC CCT GAG GTC ACA TGC GTG GTG
GGG GGT TTT GGG TTC CTG TGG GAG TAC TAG AGG GCC TGG GGA CTC CAG TGT ACG CAC CAC
Pro Pro Lys Pro Lys Asp Thr Leu Met Ile Ser Arg Thr Pro Glu Val Thr Cys Val Val
381_____385_____hFC DOMAIN_____395_____400
```

TABLE 2-continued

Valpha VF#1

```
        1210       1220       1230       1240       1250       1260
          *          *          *          *          *          *
GTG GAC GTG AGC CAC GAA GAC CCT GAG GTC AAG TTC AAC TGG TAC GTG GAC GGC GTG GAG
CAC CTG CAC TCG GTG CTT CTG GGA CTC CAG TTC AAG TTG ACC ATG CAC CTG CCG CAC CTC
Val Asp Val Ser His Glu Asp Pro Glu Val Lys Phe Asn Trp Tyr Val Asp Gly Val Glu
401_____405_____hFC DOMAIN_____415_____420

1270       1280       1290       1300       1310       1320
          *          *          *          *          *          *
GTG CAT AAT GCC AAG ACA AAG CCG CGG GAG GAG CAG TAC AAC AGC ACG TAC CGT GTG GTC
CAC GTA TTA CGG TTC TGT TTC GGC GCC CTC CTC GTC ATG TTG TCG TGC ATG GCA CAC CAG
Val His Asn Ala Lys Thr Lys Pro Arg Glu Glu Gln Tyr Asn Ser Thr Tyr Arg Val Val
421_____425_____hFC DOMAIN_____435_____440

1330       1340       1350       1360       1370       1380
          *          *          *          *          *          *
AGC GTC CTC ACC GTC CTG CAC CAG GAC TGG CTG AAT GGC AAG GAG TAC AAG TGC AAG GTC
TCG CAG GAG TGG CAG GAC GTG GTC CTG ACC GAC TTA CCG TTC CTC ATG TTC ACG TTC CAG
Ser Val Leu Thr Val Leu His Gln Asp Trp Leu Asn Gly Lys Glu Tyr Lys Cys Lys Val
441_____445_____hFC DOMAIN_____455_____460

1390       1400       1410       1420       1430       1440
          *          *          *          *          *          *
TCC AAC AAA GCC CTC CCA GCC CCC ATC GAG AAA ACC ATC TCC AAA GCC AAA GGG CAG CCC
AGG TTG TTT CGG GAG GGT CGG GGG TAG CTC TTT TGG TAG AGG TTT CGG TTT CCC GTC GGG
Ser Asn Lys Ala Leu Pro Ala Pro Ile Glu Lys Thr Ile Ser Lys Ala Lys Gly Gln Pro
461_____465_____hFC DOMAIN_____475_____480

1450       1460       1470       1480       1490       1500
          *          *          *          *          *          *
CGA GAA CCA CAG GTG TAC ACC CTG CCC CCA TCC CGG GAG GAG ATG ACC AAG AAC CAG GTC
GCT CTT GGT GTC CAC ATG TGG GAC GGG GGT AGG GCC CTC CTC TAC TGG TTC TTG GTC CAG
Arg Glu Pro Gln Val Tyr Thr Leu Pro Pro Ser Arg Glu Glu Met Thr Lys Asn Gln Val
481_____485_____hFC DOMAIN_____495_____500

1510       1520       1530       1540       1550       1560
          *          *          *          *          *          *
AGC CTG ACC TGC CTG GTC AAA GGC TTC TAT CCC AGC GAC ATC GCC GTG GAG TGG GAG AGC
TCG GAC TGG ACG GAC CAG TTT CCG AAG ATA GGG TCG CTG TAG CGG CAC CTC ACC CTC TCG
Ser Leu Thr Cys Leu Val Lys Gly Phe Tyr Pro Ser Asp Ile Ala Val Glu Trp Glu Ser
501_____505_____hFC DOMAIN_____515_____520

1570       1580       1590       1600       1610       1620
          *          *          *          *          *          *
AAT GGG CAG CCG GAG AAC AAC TAC AAG ACC ACG CCT CCC GTG CTG GAC TCC GAC GGC TCC
TTA CCC GTC GGC CTC TTG TTG ATG TTC TGG TGC GGA GGG CAC GAC CTG AGG CTG CCG AGG
Asn Gly Gln Pro Glu Asn Asn Tyr Lys Thr Thr Pro Pro Val Leu Asp Ser Asp Gly Ser
521_____525_____hFC DOMAIN_____535_____540

1630       1640       1650       1660       1670       1680
          *          *          *          *          *          *
TTC TTC CTC TAC AGC AAG CTC ACC GTG GAC AAG AGC AGG TGG CAG CAG GGG AAC GTC TTC
AAG AAG GAG ATG TCG TTC GAG TGG CAC CTG TTC TCG TCC ACC GTC GTC CCC TTG CAG AAG
Phe Phe Leu Tyr Ser Lys Leu Thr Val Asp Lys Ser Arg Trp Gln Gln Gly Asn Val Phe
541_____545_____hFC DOMAIN_____555_____560

1690       1700       1710       1720       1730       1740
          *          *          *          *          *          *
TCA TGC TCC GTG ATG CAT GAG GCT CTG CAC AAC CAC TAC ACG CAG AAG AGC CTC TCC CTG
AGT ACG AGG CAC TAC GTA CTC CGA GAC GTG TTG GTG ATG TGC GTC TTC TCG GAG AGG GAC
Ser Cys Ser Val Met His Glu Ala Leu His Asn His Tyr Thr Gln Lys Ser Leu Ser Leu
561_____565_____hFC DOMAIN_____575_____580

1750  1755
          *     *
TCT CCG GGT AAA TGA (SEQ ID NO: 3)
AGA GGC CCA TTT ACT
Ser Pro Gly Lys *** (SEQ ID NO: 4)
581_____585
```

What is claimed is:

1. A fusion polypeptide capable of synchronously binding VEGF polypeptide and TNF polypeptide consisting of: (a) TNFR2 component and VEGFR1 component operatively linked to (b) a multimerizing component, wherein the TNFR2 component consists of a fragment of the extracellular domain of TNFR2 comprising the amino acid sequence of cysteine rich domain 1, cysteine rich domain 2, cysteine rich domain 3, and cysteine rich domain 4 of the extracellular domain of TNFR2 in order, and wherein the VEGFR1 component consists of a fragment of the extracellular domain of VEGFR1 comprising the amino acid sequence of Ig-like domain 2 of the extracellular domain of VEGFR1, excluding other Ig-like domains of the extracellular domain of VEGFR1.

2. The fusion polypeptide claim 1, wherein the amino acid sequence of cysteine rich domain 1, cysteine rich domain 2, cysteine rich domain 3, and cysteine rich domain 4 of the extracellular domain of TNFR2 are located N-terminal to the Ig-like domain 2 of the extracellular domain of VEGFR1.

3. The fusion polypeptide of claim 1, wherein the amino acid sequence of cysteine rich domain 1, cysteine rich domain 2, cysteine rich domain 3, and cysteine rich domain 4 of the extracellular domain of TNFR2 are located C-terminal to the Ig-like domain 2 of the extracellular domain of VEGFR1.

4. The fusion polypeptide of claim 1, wherein the multimerizing component comprises an immunoglobulin domain.

5. The fusion polypeptide of claim 4, wherein the immunoglobulin domain is selected from the group consisting of the Fc domain of IgG, the heavy chain of IgG, and the light chain of IgG.

6. The fusion polypeptide of claim 1, comprising the amino acid sequence of SEQ ID NO:2 or SEQ ID NO:4.

7. The fusion polypeptide according to claim 1, which has been modified by acetylation or pegylation.

8. A composition comprising the fusion polypeptide of claim 1, and a pharmaceutically acceptable carrier thereof.

9. An isolated nucleic acid molecule encoding a polypeptide capable of synchronously binding VEGF polypeptide and TNF polypeptide comprising: (a) a nucleotide sequence encoding a TNFR2 component and VEGFR1 component operatively linked to (b) a nucleotide sequence encoding a multimerizing component, wherein the TNFR2 component consists of a fragment of the extracellular domain of TNFR2 comprising the amino acid sequence of cysteine rich domain 1, cysteine rich domain 2, cysteine rich domain 3, and cysteine rich domain 4 of the extracellular domain of TNFR2 in order, and wherein the VEGFR1 component consists of a fragment of the extracellular domain of VEGFR1 comprising the amino acid sequence of Ig-like domain 2 of the extracellular domain of VEGFR1, excluding other Ig-like domains of the extracellular domain of VEGFR1.

10. The isolated nucleic acid molecule of claim 9, wherein the nucleotide sequence encoding the cysteine rich domain 1, cysteine rich domain 2, cysteine rich domain 3, and cysteine rich domain 4 of the extracellular domain of TNFR2 are located upstream of the nucleotide sequence encoding the Ig-like domain 2 of the extracellular domain of VEGFR1.

11. The isolated nucleic acid molecule of claim 9, wherein the nucleotide sequence encoding cysteine rich domain 1, cysteine rich domain 2, cysteine rich domain 3, and cysteine rich domain 4 of the extracellular domain of TNFR2 are located downstream of the nucleotide sequence encoding the Ig-like domain 2 of the extracellular domain of VEGFR1.

12. An isolated nucleic acid molecule comprising the nucleotide sequence of (a) SEQ ID NO:1 or (b) SEQ ID NO:3, or the nucleotide sequence which, as a result of the degeneracy of the genetic code, differs from the nucleotide sequence of (a) or (b) but which encodes identical amino acid sequence as expressed therefrom.

13. A vector which comprises the nucleic acid molecule of claim 9.

14. A host-vector system for the production of a fusion polypeptide which comprises the expression vector of claim 13, in a suitable recombinant host cell.

15. A method of producing a fusion polypeptide which comprises growing cells of the host-vector system of claim 14, under conditions permitting production of the fusion polypeptide and recovering the fusion polypeptide so produced.

16. A method of inhibiting VEGF receptor ligand and TNF receptor ligand activities in a mammal comprising administering to the mammal an effective amount of the fusion polypeptide of claim 1.

17. A method of decreasing or inhibiting plasma leakage in a mammalian retina comprising administering to the mammal an effective amount of the fusion polypeptide of claim 1.

18. A method of treating retinopathy in a subject suffering from retinopathy, comprising administering an effective amount of the fusion polypeptide of claim 1 to the subject.

19. A method of treating rheumatoid arthritis in a subject suffering from rheumatoid arthritis, comprising administering an effective amount of the fusion polypeptide of claim 1 to the subject.

* * * * *